(12) United States Patent
Sondermann et al.

(10) Patent No.: US 10,407,499 B2
(45) Date of Patent: Sep. 10, 2019

(54) ANTI-FC-GAMMA RECEPTOR IIB ANTIBODIES AND USES THEREOF

(71) Applicant: SuppreMol GmbH, Martinsried/München (DE)

(72) Inventors: Peter Sondermann, Stockdorf (DE); Thomas Pohl, Neuried (DE); Dominik Ter Meer, Munich (DE); Anna Carle, Munich (DE); Daniela Ehehalt, Munich (DE); Nicole Rieth, Munich (DE)

(73) Assignee: SUPPREMOL GMBH, Martinsried/Munich (DE)

( * ) Notice: Subject to any disclaimer, the term of this patent is extended or adjusted under 35 U.S.C. 154(b) by 281 days.

(21) Appl. No.: 14/912,064

(22) PCT Filed: Aug. 13, 2014

(86) PCT No.: PCT/EP2014/002234
§ 371 (c)(1),
(2) Date: Feb. 12, 2016

(87) PCT Pub. No.: WO2015/022077
PCT Pub. Date: Feb. 19, 2015

(65) Prior Publication Data
US 2016/0185857 A1    Jun. 30, 2016

(30) Foreign Application Priority Data

Aug. 16, 2013 (EP) .................................... 13004094

(51) Int. Cl.
| | |
|---|---|
| *C07K 16/00* | (2006.01) |
| *C12P 21/08* | (2006.01) |
| *A61K 39/395* | (2006.01) |
| *A61K 39/40* | (2006.01) |
| *A61K 39/42* | (2006.01) |
| *C07K 16/28* | (2006.01) |
| *C07K 1/00* | (2006.01) |
| *A61K 39/00* | (2006.01) |

(52) U.S. Cl.
CPC ............ *C07K 16/28* (2013.01); *C07K 16/283* (2013.01); *A61K 2039/505* (2013.01); *C07K 2317/24* (2013.01); *C07K 2317/33* (2013.01); *C07K 2317/56* (2013.01); *C07K 2317/565* (2013.01); *C07K 2317/70* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,849,719 B2 | 2/2005 | Shi et al. | |
| 7,504,482 B2 | 3/2009 | Sondermann et al. | |
| 8,853,363 B2 | 10/2014 | Huber et al. | |
| 2005/0002924 A1 | 1/2005 | Huber et al. | |
| 2014/0120080 A1 | 5/2014 | Buckel et al. | |
| 2015/0274804 A1 | 10/2015 | Sondermann et al. | |
| 2017/0226208 A1 | 8/2017 | Carle et al. | |

FOREIGN PATENT DOCUMENTS

| | | |
|---|---|---|
| EP | 1870422 A1 | 12/2007 |
| WO | 2000/032767 A1 | 6/2000 |
| WO | 2003/043648 A2 | 5/2003 |
| WO | 2004/016750 A2 | 2/2004 |
| WO | 2005/051999 A2 | 6/2005 |
| WO | 2007/068047 A1 | 6/2007 |
| WO | 2009/062690 A1 | 5/2009 |
| WO | 2009/083009 A2 | 7/2009 |
| WO | 2009/158696 A1 | 12/2009 |
| WO | 2014/068012 A1 | 5/2014 |
| WO | 2015/022077 A1 | 2/2015 |

OTHER PUBLICATIONS

Janeway et al., Immunology Third Edition, Garland Publishing Inc. 1997, Chapter 3, Structure of the Antibody Molecule and Immunoglobulin Genes, pp. 3:1-3:11, see entire selection (Year: 1997).*
Rudikoff et al., PNAS. 1982 vol. 79 p. 1979-83. (Year: 1982).*
Mathey et al. Eur. J. Immunol. 2004. 34:2065-2071 (Year: 2004).*
Ahn et al., Long-term danazol therapy in autoimmune thrombocytopenia: unmaintained remission and age-dependent response in women. Annals of Internal Medicine, vol. 111, pp. 723-729 (1989).
Baccarani et al., Splenectomy in hematology. Current practice and new perspectives. Haematologica, vol. 84, pp. 431-436 (1999).
Berchtold et al., Therapy of chronic idiopathic thrombocytopenic purpura in adults. Blood, vol. 74, No. 7, pp. 2309-2317 (Nov. 15, 1989).
Brighton et al., Prospective evaluation of the clinical usefulness of an antigen-specific assay (MAIPA) in the idiopathic thrombocytopenic purpura and other immune thrombocytopenias. Blood, vol. 88, No. 1, pp. 194-201 (1996).
Burzynski, Julianna, New options after first-line therapy for chronic immune thrombocytopenic purpura. American Journal of Health-System Pharmacy, vol. 66, Suppl. 2, pp. S11-S21 (2009).
Cines et al., How I treat idiopathic thrombocytopenic purpura (ITP). Blood, vol. 106, No. 7, pp. 2244-2251 (2005).
Clinical trial ISRCTN47912914, A phase Ib/IIa clinical trial to investigate the safety and efficacy of recombinant human soluble Fc-gamma receptor IIb (SM101) for intravenous application in the treatment of patients with chronic adult idiopathic thrombocytopenic purpura (ITP). ISRCTN Registry, last edited Apr. 19, 2011.

(Continued)

*Primary Examiner* — Chun W Dahle
(74) *Attorney, Agent, or Firm* — K&L Gates LLP; Louis C. Cullman; Hal Gibson

(57) ABSTRACT

The present invention provides an anti-FcγRIIB antibodies which, in comparison to prior art antibodies, markedly increase ITIM phosphorylation of FcγRIIB and can thus be used for the treatment or prophylaxis of autoimmune diseases.

12 Claims, 14 Drawing Sheets

Specification includes a Sequence Listing.

(56) References Cited

OTHER PUBLICATIONS

Commmittee for orphan medicinal Products: Public summary of positive opinion for orphan designation of recombinant human soluble FC-gamma receptor II b for the treatment of idiopathic thrombocytopenic purpura. European Medicines Agnecy, Pre-authorisation Evaluation of Medicines for Human Use (©EMEA, 2008) (Aug. 2, 2007, orphan designation (EU/3/07/462) was granted by the European Commission to SuppreMol GmbH, Germany, for recombinant human soluble Fc-gamma receptor II b for the treatment of idiopathic thrombocytopenic purpura, 4 pages).

Ellsworth et al., Recombinant soluble human FcγR1A (CD64A) reduces inflammation in murine collagen-induced arthritis. The Journal of Immunology, 182:7272-7279 (2009).

Ellsworth et al.,Targeting immune complex-mediated hypersensitivity with recombinant soluble human FcγRIA (CD64A). The Journal of Immunology, 180:580-589 (2008).

EU Clinical Trials Register, A randomised, multi-centre, double-blind, placebo-controlled, single/multiple dose escalation phase Ib/IIa clinical trial to investigate the safety and efficacy of recombinant human soluble Fc-gamma receptor IIb (SM101) for intravenous application in the treatment of patients with chronic adult idiopathic thrombocytopenic purpura (ITP) (Sep. 14, 2009).

Feudjo-Tepie et al., Prevalence of diagnosed chronic immune thrombocytopenic purpura in the US: analysis of a Large US claim database: a rebuttal. Journal of Thrombosis and Haemostasis, vol. 6, pp. 711-712 (2008).

George et al., Idiopathic thrombocytopenic purpura: A practice guideline developed by explicit methods for the American Society of Hematology. Blood, vol. 88, No. 1, pp. 3-40 (1996).

Godeau et al., Dapsone for chronic autoimmune thrombocytopenic purpura: a report of 66 cases. British Journal of Haematology, vol. 97, pp. 336-339 (1997).

Godeau et al., Treatment of adult chronic autoimmune thrombocytopenic purpura with repeated high-dose intravenous immunoglobulin. Blood, vol. 82, No. 5, pp. 1415-1421 (1993).

Guidelines for the investigation and management of idiopathic thrombocytopenic purpura in adults, children and in pregnancy. British Journal of Haematology, vol. 120, pp. 574-596 (2003).

International Search Report for International Application No. PCT/EP2013/072741 filed on Oct. 30, 2013.

Magnusson et al., Amelioration of collagen-induced arthritis by human recombinant soluble FCγRIIb. Clinical Immunology, 127:225-233 (2008).

Provan et al., Efficacy of mycophenolate mofetil as single-agent therapy for refractory immune thrombocytopenic purpura. American Journal of Hematology, vol. 81, pp. 19-25 (2006).

Rodeghiero et al., Standardization of terminology, definitions and outcome criteria in immune thrombocytopenic purpura of adults and children: report of an international working group. Blood, vol. 113, No. 11, pp. 2386-2393 (2009).

Scaradavou et al., Intravenous anti-D treatment of immune thrombocytopenic purpura: experience in 272 patients. Blood, vol. 89, No. 8, pp. 2689-2700 (1997).

Segal et al., Prevalence of immune thrombocytopenia: analyses of administrative data. Journal of Thrombosis and Haemostasis, vol. 4, pp. 2377-2383 (2006).

SuppreMol Press Release, SuppreMol releases positive interim phase Ib/IIa results on SM101 in primary immune thrombocytopenia (ITP) trials (Feb. 14, 2012, Munich, Germany).

International Search Report and Written Opinion for International Application No. PCT/EP2014/002234 filed on Aug. 13, 2014.

Janeway et al., Immunology Third Edition, Garland Publishing Inc. 1997, Chapter 3, Structure of the Antibody Molecule and Immunoglobulin Genes, pp. 122-123 (1997).

Mathey et al., Commentary: Sorting the wheat from the chaff: identifying demyelinating components of the myelin bligodendrocyte glycoprotein (MOG)-specific autoantibody repertoire. Eur. J. Immunol., 34:2065-2071 (2004).

Rudikoff et al., Single amino acid substitution altering antigen-binding specificity. PNAS, vol. 79, pp. 1979-1983 (1982).

Sondermann et al., Human FCγ receptor IIb expressed in *Escherichia coli* reveals IgG binding capability. Biological Chemistry, vol. 380, pp. 717-721 (1999).

SuppreMol Press Release, SuppreMol initiates phase Ib/IIa clinical trial with its lead candidate SM101 (Apr. 12, 2010, Munich, Germany).

SuppreMol Press Release: SuppreMol initiates Phase IIa clinical trial in Systemic Lupus Erythematosus (SLE) with its lead candidate SM101 (Jul. 11, 2011).

SuppreMol Press Release: SuppreMol Completes Successful Pre-IND meeting with FDA. (Munich, Germany, Jan. 24, 2011).

Veri et al., Monoclonal antibodies capable of discriminating the human inhibitory Fcgamma-receptor IIb (CD32B) from the activating Fcgamma-receptor IIA (CD32A): biochemical, biological and functional characterization. Immunology, vol. 121, pp. 392-404 (2007).

\* cited by examiner

SPR analysis of humanized 8A6 WT and N297A variants, GB3 WT and ch8A6 WT

| | $k_{off}$ [s$^{-1}$] |
|---|---|
| hu8A6_wt | $9.5 \times 10^{-4}$ |
| hu8A6_N297A | $8.8 \times 10^{-4}$ |
| ch8A6_wt | $4.9 \times 10^{-4}$ |
| chGB3_N297A | $1 \times 10^{-2}$ |

Figure 1: Surface Plamon Resonance analysis of humanized 8A6 (hu8A6_VH10+VL6) according to SEQ. ID. No. 3 and 4 in either Wildtype or N297A format, ch8A6_WT (according to SEQ. ID. NO. 1 and 2) and chGB3_N297A.

Sequence of hu8A6_wt and hu8A6-N297A

The aminoacids of the variable regions are just numbered regardless to any numbering scheme. For a better understanding of the aminoacid changes in the Fc-domain the EU-numbering was chosen.

Heavy chain / humanized 8A6_wt (glycosylated)

VH domain (variant VH10)

```
1  QVQLVESGGG VVQPGRSLRL SCAASGFTFS DYYMAWVRQA PGKGLEWVAS ISYDGSNKYY
61 GDSVKGRFTI SRDNSKNTLY LQMNSLRAED TAVYYCARPG DYWGQGTLVT VSS (SEQ ID
NO. 3)
```

Fc-domain (glycosylated N297 / allotyp G1m17 containing K214; E356; M358; A431 / without C-terminal Lys; according to Eu-numbering)

```
118 ASTKGPSVFP LAPSSKSTSG GTAALGCLVK DYFPEPVTVS WNSGALTSGV HTFPAVLQSS
178 GLYSLSSVVT VPSSSLGTQT YICNVNHKPS NTKVDKKVEP KSCDKTHTCP PCPAPELLGG
238 PSVFLFPPKP KDTLMISRTP EVTCVVVDVS HEDPEVKFNW YVDGVEVHNA KTKPREEQYN
298 STYRVVSVLT VLHQDWLNGK EYKCKVSNKA LPAPIEKTIS KAKGQPREPQ VYTLPPSREE
358 MTKNQVSLTC LVKGFYPSDI AVEWESNGQP ENNYKTTPPV LDSDGSFFLY SKLTVDKSRW
418 QQGNVFSCSV MHEALHNHYT QKSLSLSPG-  (SEQ ID NO. 6)
```

Heavy chain / humanized 8A6_N297A (deglycosylated)

VH domain see above

Fc-domain (N297A variant / allotyp G1m17 containing K214; E356; M358; A431 / without C-terminal Lys; according to Eu-numbering)

```
118 ASTKGPSVFP LAPSSKSTSG GTAALGCLVK DYFPEPVTVS WNSGALTSGV HTFPAVLQSS
178 GLYSLSSVVT VPSSSLGTQT YICNVNHKPS NTKVDKKVEP KSCDKTHTCP PCPAPELLGG
238 PSVFLFPPKP KDTLMISRTP EVTCVVVDVS HEDPEVKFNW YVDGVEVHNA KTKPREEQYA
298 STYRVVSVLT VLHQDWLNGK EYKCKVSNKA LPAPIEKTIS KAKGQPREPQ VYTLPPSREE
358 MTKNQVSLTC LVKGFYPSDI AVEWESNGQP ENNYKTTPPV LDSDGSFFLY SKLTVDKSRW
418 QQGNVFSCSV MHEALHNHYT QKSLSLSPG-  (SEQ ID NO. 28)
```

Figure 2: Sequences of hu8A6_wt and hu8A6_N297A variants showing position of N to A aminoacid modification in N297A format

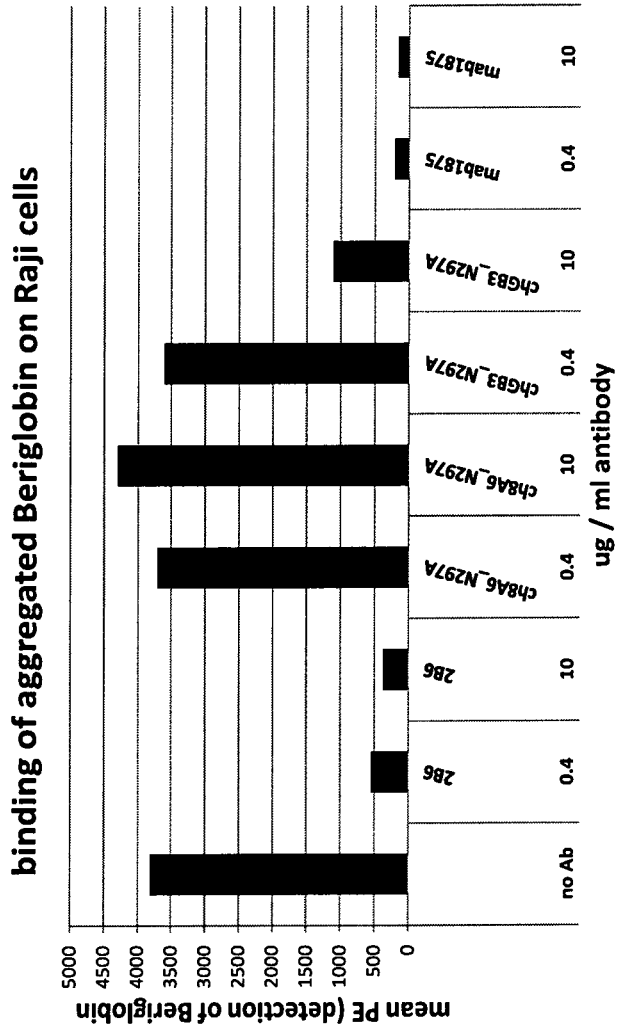
Figure 3: Non-blocking characteristic of ch8A6_N297A. Raji cells were incubated with a set amount of aggregated human IgG and varying amounts of ch8A6_N297A, chGB3_N297A or blocking antibodies 2B6 or mab1875 (R&D). The antibodies according to the invention are non-blocking.

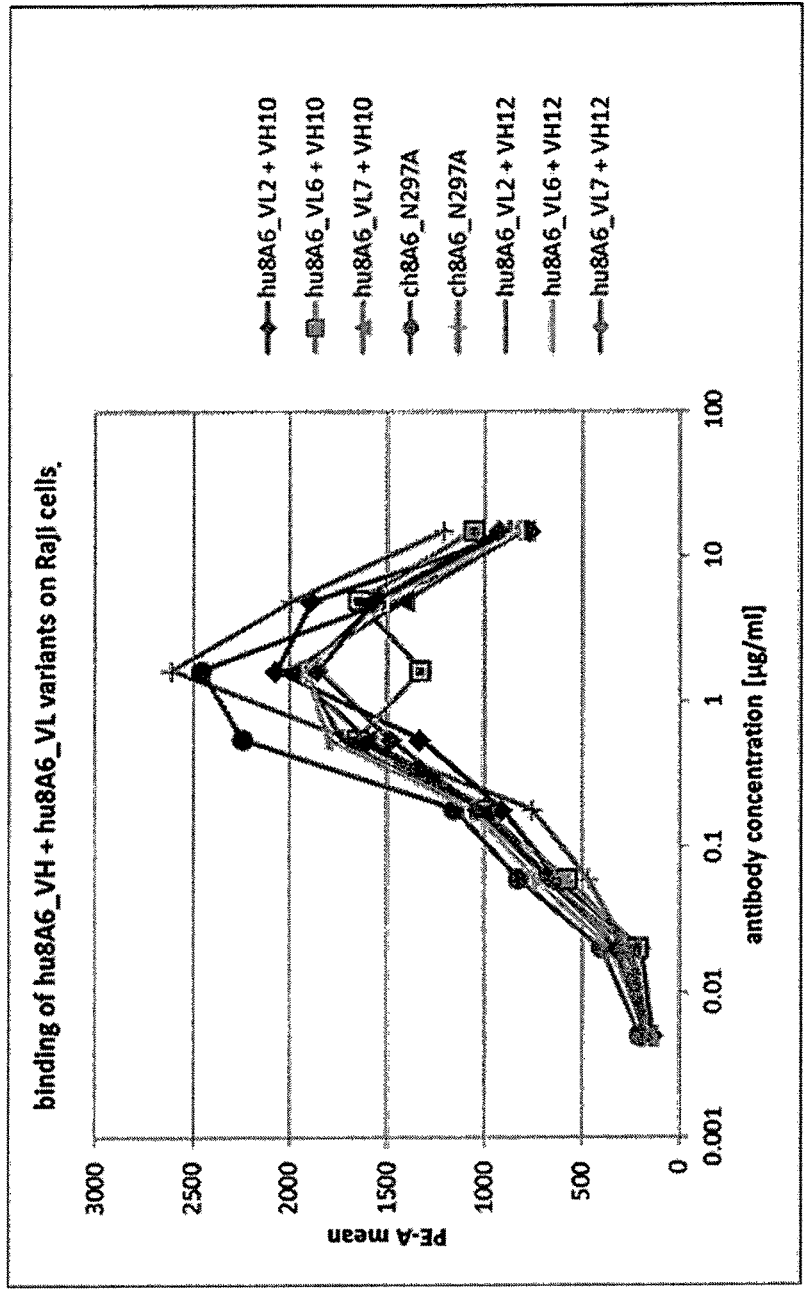
Figure 4: Binding from 15 μg/ml to 0.005 μg/ml of Protein A purified antibody (hu8A6_VL + hu8A6_VH and ch8A6_N297A to native FcγRIIB expressed on Raji cells. Humanized 8A6 variants bind with high avidity to FcγRIIB expressed on Raji cells.

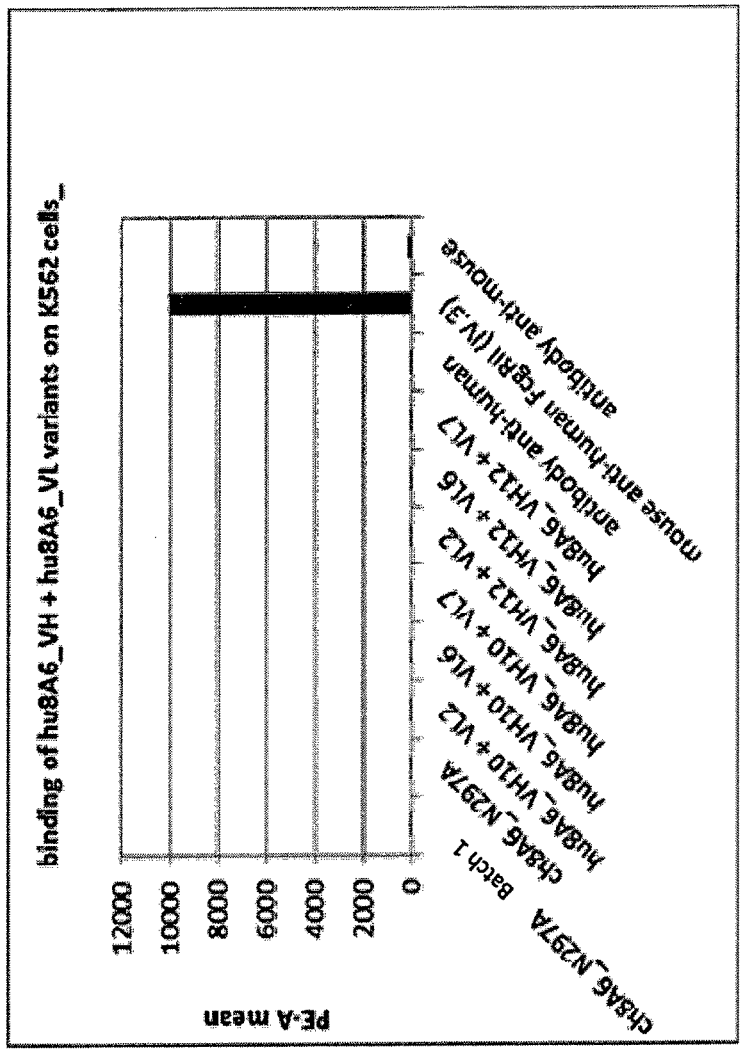
Figure 5: Binding of 15 μg/ml of Protein A purified antibody (hu8A6_VH + hu8A6_VL and ch8A6_N297A) and ch8A6_N297A to native FcγRIIA expressed on K562 cells. Antibodies according to the invention do not bind to FcγRIIA on K-562.

ITIM-Phosphorylation increased by ch8A6 in PBMC from healthy donor

Figure 6 a:
ITIM-Phosphorylation Assay. PBMC from healthy donor were isolated using Ficoll seperation and subsequently left untreated or incubated for 25 minutes with an antibody mix containing anti-IgM (anti-human, mouse) and anti-mouse IgG (rabbit). Subsequently the cells were either treated 20 minutes with 5µg/mL ch8A6_N297A or buffer as control (w/o). Cells were harvested after incubation and lysed according to protocol. Lysates were subjected to WB-analysis. ß-Actin = loading control.

Figure 6 b:
Control experiment for ITIM-Phosphorylation. Daudi cells were left untreated or treated for 25 minutes with an isotype control antibody, polyclonal anti-human anti-IgM (polycl. anti-hIgM), monoclonal anti human IgM (anti-hIgM), anti-hIgM + 5µg/mL ch8A6_N297A, anti-mouse IgG from rabbit (amouseIgG), amouseIgG+5µg/mL ch8A6, mix of anti-hIgM and amouseIgG (Ab mix) or Ab mix + 5µg/mL ch8A6_N297A). ß-Actin = loading control.

Figure 6c:
8A6 (wt) as well as hu8A6 showed strong phosphorylation of Fcgamma RIIB without the need of preceding coligation of BCR and FcgRIIB. After crosslinking of the receptors by the antibody mix, 8A6 (wt) and hu8A6 were - as expected - able to induce ITIM phosphorylation

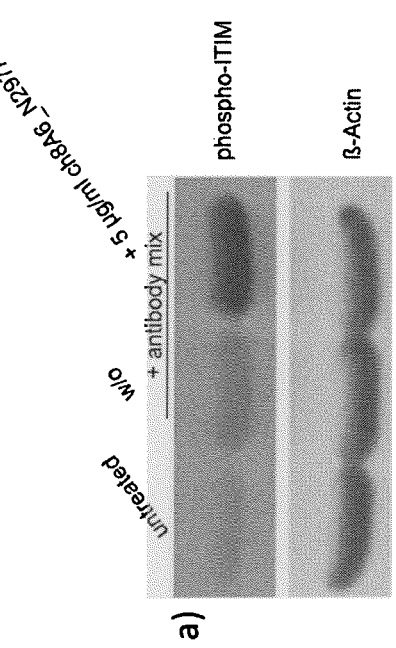

a)

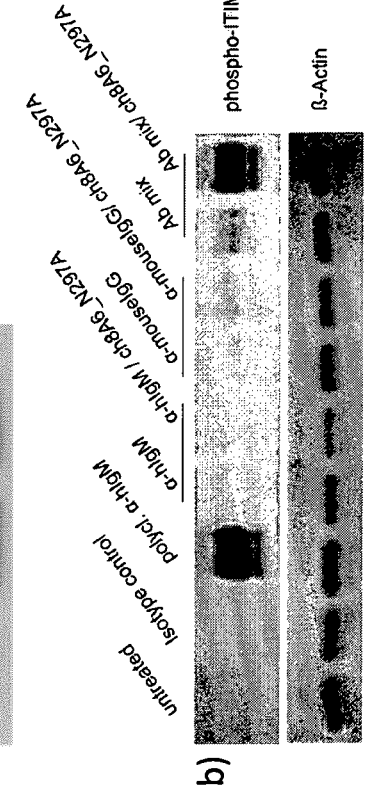

b)

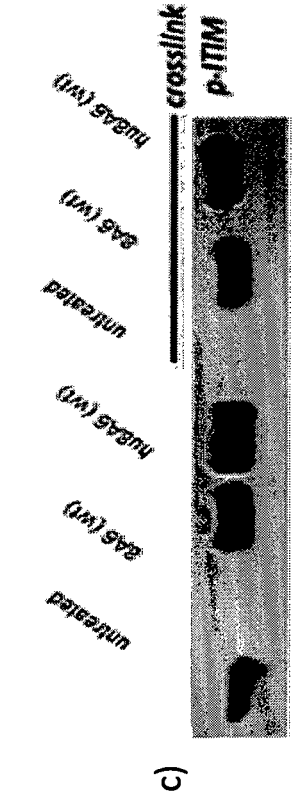

c)

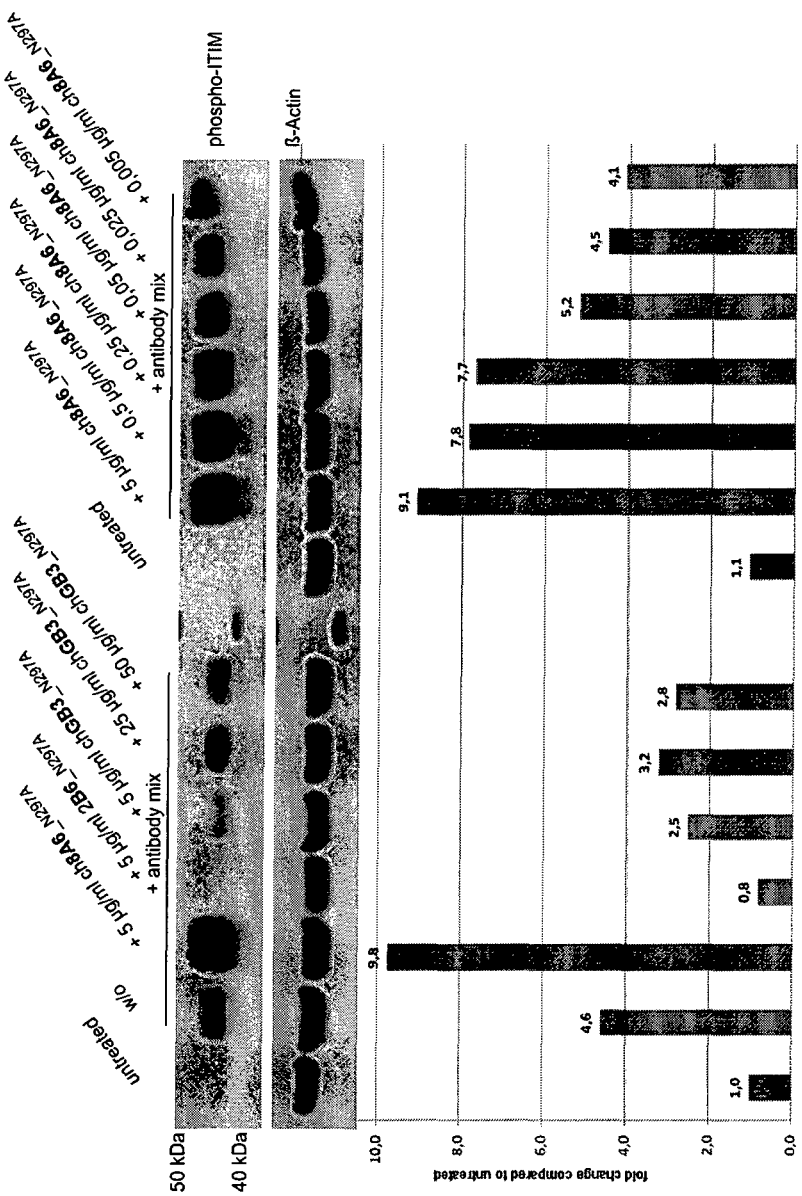

Figure 7:
ITIM-Phosphorylation Assay. Daudi cells left were either left untreated or incubated for 25 minutes with an antibody mix containing anti-IgM (anti-human, mouse) and anti-mouse IgG (rabbit). Subsequently the cells were either treated 20 minutes with varying amounts of chGB3_N297A or ch8A6_N297A or buffer as control (w/o). Cells were harvested after incubation and lysed according to protocol. Lysates were subjected to WB-analysis. ß-Actin = loading control.

Comparison of the effect of the humanized variant hu8A6_N297A and chGB3_N297A and ch8A6_N297A on ITIM phosphorylation in primary PBMCs

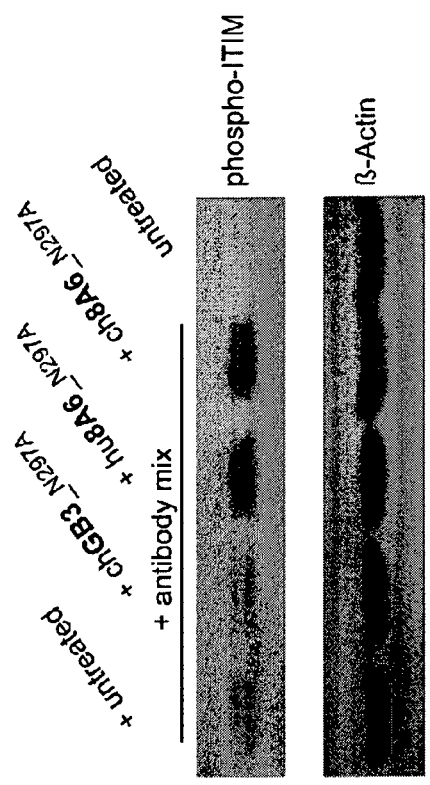

Figure 8: Comparison of the effect of the humanized variant hu8A6_N297A and chGB3_N297A and ch8A6_N297A on ITIM phosphorylation in primary PBMCs. After crosslinking of BCR and FcgRIIB by the antibody mix, the different antibodies were added at 5 µg/ml and Western Blot analysis for ITIM phosphorylation was conducted. ß-Actin = loading control.

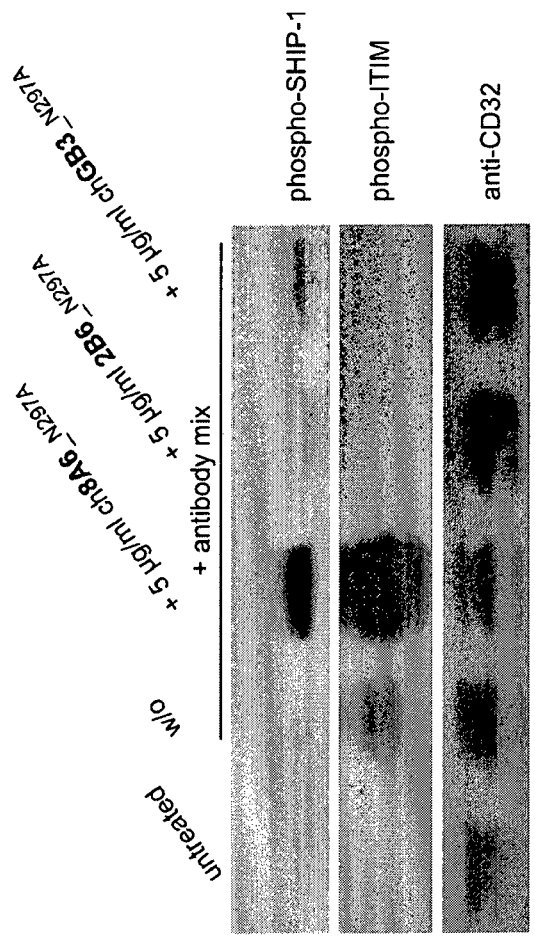

Figure 9: Co-Immunoprecipitation of phosphorylated SHIP-1 with FcγRIIB ITIM. After stimulation of Daudi cells with the antibody mix and either ch8A6_N297A, blocking anti-FcγRIIB antibody 2B6 or chGB3_N297A (5μg/mL), FcγRIIB was precipitated from cell lysates and Western Blot analysis was performed for the phosphatase SHIP-1. anti-CD32 using pan anti-CD32 antibody (AF1330) = loading control.

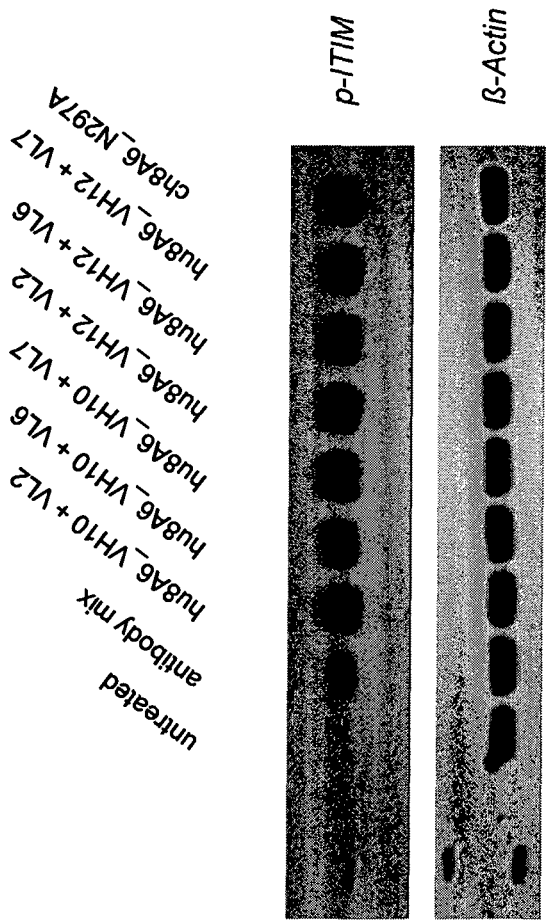

Figure 10:
ITIM-Phosphorylation Assay. Daudi cells were left incubated for 25 minutes with buffer (untreated) or a mix (antibody mix) containing anti-IgM (anti-human, mouse) and anti-mouse IgG (rabbit). Subsequently the cells were either treated 20 minutes with 0.25µg/mL of ch8A6_N297A or humanized 8A6 variants hu8A6_VH10+VL2/VH10+VL6/ VH10+VL7/VH12+VL2/VH12+VL6/VH12+VL7. Cells were harvested after incubation and lysed according to protocol. Lysates were subjected to WB-analysis. ß-Actin = loading control.

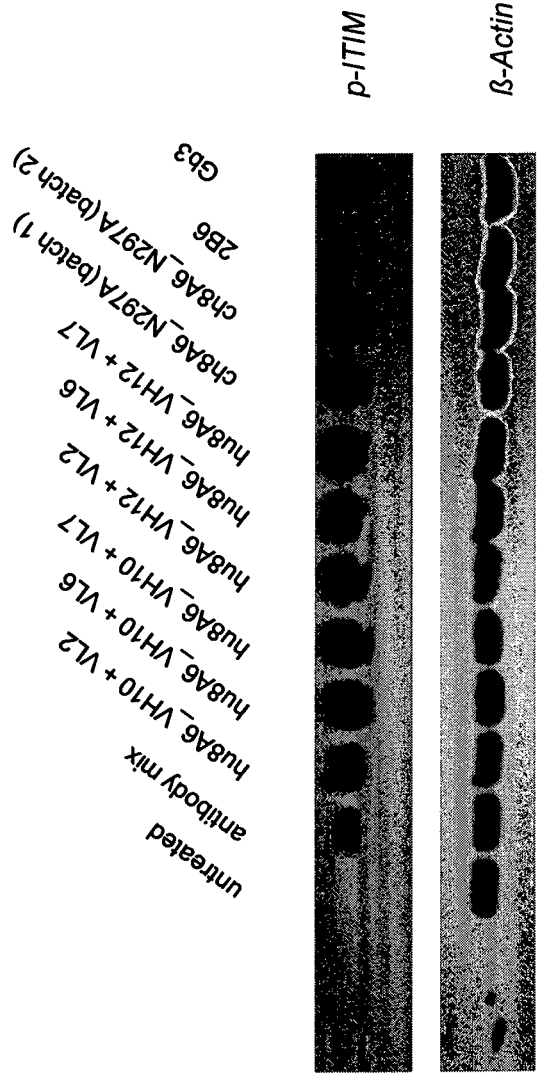

Figure 11:
ITIM-Phosphorylation Assay. Daudi cells were left incubated for 25 minutes with buffer (untreated) or a mix (antibody mix) containing anti-IgM (anti-human, mouse) and anti-mouse IgG (rabbit). Subsequently the cells were either treated 20 minutes with 0.25μg/mL of ch8A6_N297A, humanized 8A6 variants hu8A6_VH10+VL2/VH10+VL6/ VH10+VL7/VH12+VL2/VH12+VL6/VH12+VL7, blocking 2B6 or chGB3_N297A. Cells were harvested after incubation and lysed according to protocol. Lysates were subjected to WB-analysis. ß-Actin = loading control.

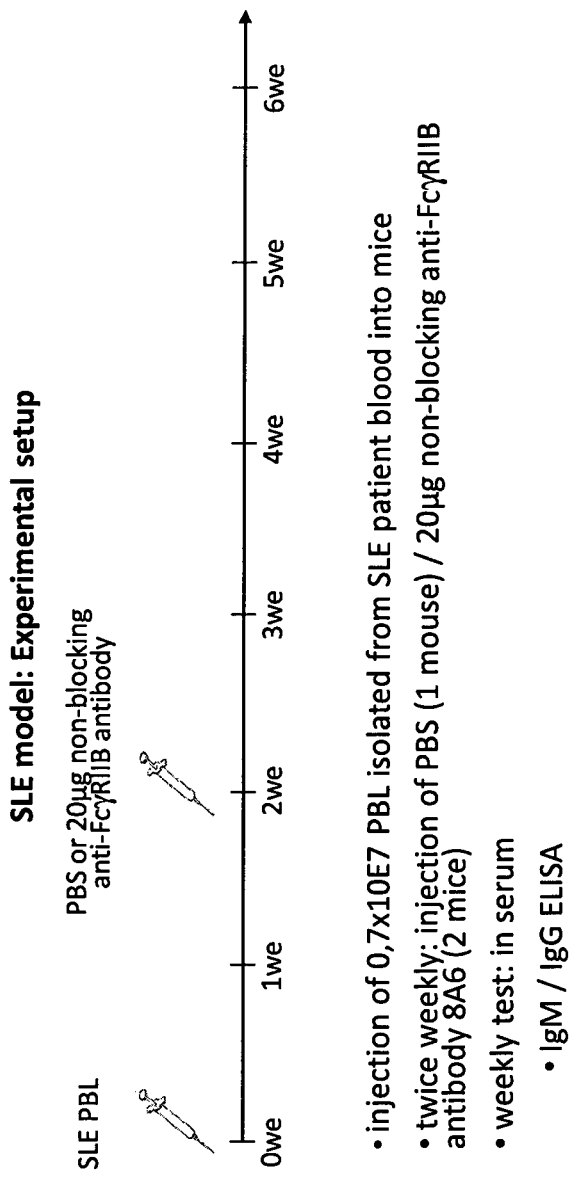
Figure 12: Experimental setup for SLE-PBL mouse model. PBL from human SLE patients are transfered into immuno-compromised mice. PBL cells are engrafted and mice are subsequently treated with control (PBS) or anti-FcγRIIb ch8A6_N297A antibody according to the invention.

Total human IgG level [μg/mL] in mice grafted with PBL from human donors suffering from SLE. Depicted are mice treated with control (#2, PBS) or chimeric 8A6 = ch8A6_N297A (#3 and #4, anti-FcγRIIB antibody, N297A-Format). No significant difference in total human IgG between PBS or anti-FcγRIIB.

Reduction of disease specific human anti-DNA IgG in ch8A6_N297A treated mice starting week 4 post SLE-PBL transfer/grafting. Depicted are anti-DNA IgG titers in two different mice, #3 and #4 (treated with ch8A6_N297A), #2 shows PBS control

ANTI-FC-GAMMA RECEPTOR IIB ANTIBODIES AND USES THEREOF

FcγRII receptors, members of the immunoglobulin gene superfamily of proteins, are single polypeptide chain 40 kDa integral membrane-bound glycoproteins comprised of two extracellular immunoglobulin domains, a single membrane-spanning domain and a cytoplasmatic domain of varying length. FcγRII receptors are expressed on a variety of haemapoietic cells and are the only Fc-receptors on human platelets and megakaryocytes (Cassel, McKenzie, 1993). Three FcγRII receptor types are known in humans, FcγRIIA, FcγRIIB and FcγRIIC, which all bind IgG (e.g. $IgG_1$ with an affinity of $1$-$2\times10^6 M^{-1}$) or immune complexes (ICs, e.g. IgG opsonized pathogens). FcγRIIA and FcγRIIB vary from each other mainly due to differences in the cytoplasmatic domains which ultimately lead to functionally heterogeneous responses upon receptor ligation. FcγRIIA triggering leads to activation of the cell (e.g. phagocytosis, respiratory burst) and FcγRIIB initiates inhibitory signals resulting e.g. in the inhibition of B cell activation. FcγRIIC shares the extracellular domain of FcγRIIB and the cytoplasmatic domain of FcγRIIA, thus transferring activatory signals upon binding of IgG or ICs. FcγRIIB is expressed on all leukocytes with the exception of T- and NK-cells and is the sole inhibitory Fc receptor expressed on human B cells. Monocytes, macrophages, dendritic cells, basophils and mast cells co-express the activating FcγRIIA and the inhibitory FcγRIIB receptor and FcγRIIC is expressed on natural killer cells (NK cells) and constitutes the only FcγR on this cell type. Two isoforms are known for FcγRIIB that differ in their biological function. FcγRIIB-1 is exclusively expressed on B cells, whereas FcγRIIB-2, which elicits the induction of endo-/phagocytosis upon IC binding, is found on all other FcγRIIB expressing cells (Nimmerjahn, Ravetch, 2008).

FcγRIIB shares a 93% homology in the extracellular region with FcγRIIA. As stated above, the main difference between FcγRIIA and FcγRIIB is found in the cytoplasmatic domain. While FcγRIIA comprises an ITAM (immunoreceptor tyrosine-based activatory motif), FcγRIIB comprises an ITIM (immunoreceptor tyrosine-based inhibitory motif).

FcγRIIA clustering via binding of ICs leads to co-localization of the ITAM motif with receptor-associated kinases effecting the phosphorylation of tyrosine residues in the ITAM motif (consensus sequence: $Y$-$X_2$-$L$/$I$-$X_8$-$Y$-$X_2$-$L$/$I$, Isakov, 1997) and subsequent interaction with the kinase Syk, which effects the activation of the cell via numerous downstream signaling and gene activation events (Ghazizadeh et al., 1994). Immonuglobulin binding to the activatory FcγRIIA elicits a pro-inflammatory response which subsequently leads to the removal of pathogens but in case of auto-antibody can also lead to the destruction of healthy tissues peaking in pathological auto-immune disease. Thus a tight control of antibody specificity and a negative feedback system is needed to circumvent aberrant damage to the body by the immune system. The inhibitory FcγRIIB receptor is part of this negative feedback system.

FcγRIIB is characterized by the presence of an ITIM motif (consensus sequence: $V$/$I$-$X$-$Y$-$X_2$-$V$/$L$, Isakov, 1997) in the cytoplasmatic domain, which is phosphorylated by the kinase Lyn upon binding of Ig-aggregates or ICs and co-ligation with ITAM-bearing activatory Fcγ receptors. The phosphorylated ITIM attracts the SH2-domain of the inositol polyphosphate 5'-phosphatase (SHIP), which in turn hydrolyzes phosphoinositol messengers released as a consequence of ITAM-containing FcγR-mediated tyrosine kinase activation, consequently preventing influx of intracellular $Ca^{2+}$. Cross-linking of FcγRIIB inhibits the activating response to FcγR ligation which in turn inhibits B cell activation, proliferation and antibody secretion.

FcγRIIB has two inhibitory activities. As mentioned above, one of these is dependent on the ITIM motif and occurs when FcγRIIB is ligated to an ITAM-carrying receptor (e.g. FcγRIIA) resulting in the inhibition of ITAM-triggered calcium mobilization and cellular proliferation. This means that calcium-dependent processes such as degranulation, phagocytosis, ADCC, cytokine release and pro-inflammatory activation, and also B cell proliferation are blocked by FcγRIIB. The second inhibitory activity of FcγRIIB involves homo-aggregation of the receptor on B cells (FcγRIIB clustering). Homo-aggregation delivers a pro-apoptotic signal into the cytoplasma which can be blocked by ligation of FcγRIIB to the B cell receptor (BCR). BCR signaling post multivalent-antigen binding is characterized by the phosphorylation of the clustered BCR by Lyn, a kinase of the Src-family. This Lyn-effected phosphorylation concurs with the association of the BCR with sphingolipid- and cholesterol-rich membrane microdomains that are called lipid rafts. These insoluble lipid rafts play an important role in the formation of the immune synapse. It has been observed, that BCR interaction with antigen on an APC (antigen presenting cell) leads to the formation of this immune synapse at the interface of the engaged B cell and APC. The co-ligation of FcγRIIB with the BCR destabilizes the association of the BCR with lipid rafts, subsequently blocking the formation of the B cell's immune synapse. FcγRIIB inhibition of the BCR signaling involves the phosphorylation of the tyrosine residues in the ITIM of the cytoplasmatic domain of the receptor by the kinase Lyn and the subsequent recruitment of the inositol phosphatase SHIP (Daeron et al., 1995, Ravetch and Bolland, 2001).

It is accepted by the scientific community, that FcγRIIB can be considered as a late checkpoint during peripheral B cell development and that it also directly regulates plasma-cell survival. Thus FcγRIIB is considered to be a valuable target for the treatment of B cell disorders and especially B cell mediated immune responses.

Studies in mice and humans have already elucidated the influence of FcγRIIB on B cell activity and humoral tolerance, wherein a decreased or missing expression of FcγRIIB resulted in the development or aggravation of manifested auto-immune diseases. Indeed, FcγRIIB plays a key role in the development and course of autoimmune diseases such as Primary Immune Thrombocytopenia, Systemic Lupus Erythematosus, Rheumatoid Arthritis (RA), Pemphigus bullosus, Pemphigus vulgaris and other Pemphigus forms, B-cell driven Multiple Sclerosis, and other autoimmune diseases characterized by the development of pathogenous immune complexes. During an immune reaction in a healthy individual, pathogens that have entered the blood circulation are opsonized by antibodies (immunoglobulins, Igs) directed against epitopes of the pathogenic organisms which in turn leads to the formation of so called immune complexes. These immune complexes are subsequently phagocytized by specific cells of the immune system (e.g. macrophages, neutrophils, phagocytes) which leads to a clearance of the pathogenic organisms from the blood circulation. It was also shown, that FcγRIIB plays a pivotal role in peripheral tolerance since FcγRIIB knock-out mice develop spontaneous autoimmune diseases. Deficiencies in FcγRIIB lead to susceptibility to induced autoimmune disease (Bolland and Ravetch, 2000).

In patients suffering from autoimmune disease, expression of FcγRIIB on B cells is usually subdued or reduced in comparison to healthy persons. Whereas for example naïve B cells show normal FcγRIIB expression, memory B cells and plasma blasts from RA patients show reduced expression of this receptor (Catalán, 2010). Xiang and colleagues also were able to show that cross-linking of FcγRIIB on plasma blasts from healthy donors via surface coupled anti-FcγRIIB antibody 2.4G2 leads to apoptosis (Xiang et al., 2007).

Based on the obvious role of FcγRIIB in autoimmune diseases as described above, antibodies against the receptor have been developed in order to be able to treat or diagnose patients. WO 2009/083009 discloses antibodies against both isoforms of FcγRIIB, while WO 2004/016750 discloses antibodies that specifically bind the extracellular domain of FcγRIIB endogenously expressed on a human cell with an at least 10 times greater affinity that such antibodies bind FcγRIIA expressed on a human cell, bearing in mind that the extracellular domain of FcγRIIB and FcγRIIA shares a high degree of identity. EP 1 709 073 discloses antibodies which are highly specific for FcγRIIB and their use for the diagnosis and treatment of autoimmune diseases, infections, tumors and other abnormal conditions.

For such purpose, it is highly desirable to use antibodies with high specificity and affinity for the receptor. Especially a high specificity reduces the risk of cross-reactions of the antibody and thereby of adverse side-effects and a high affinity increases effectiveness and efficacy of its application. It is also desirable that such antibodies are non-blocking, i.e. that their binding to the Fc receptor via their variable region does not interfere with the binding of immune complexes (ICs) or aggregated IgG to the cells. Furthermore, a highly desirable advantageous property of an antibody against FcγRIIB is that it affects the FcγRIIB inhibitory coupling mechanism to control B cell activation. Namely, it is known that the intracellular part of FcγRIIB contains a so-called ITIM and that signalling through ITIM-bearing receptors is usually inhibitory in the regulation of the immune system. As described above, FcγRIIB is known to have in inhibitory regulatory function when bound by the Fc portion of IgG molecules. Hence, it is desirable to exploit the inhibitory regulatory function of FcγRIIB with the aim of controlling B cells which are involved, inter alia, in autoimmune diseases.

All in all, although the prior art already disclosed several anti-FcγRIIB antibodies with different specificities and affinities, there was still a demand for improved anti-FcγRIIB antibodies to be used in the treatment, prophylaxis and diagnosis of autoimmune diseases in a subject.

The present application satisfies this demand by the provision of the antibodies described herein below, characterized in the claims and illustrated by the appended Examples and Figures.

Much to their surprise, the present inventors observed that antibodies provided by the present invention markedly increase ITIM phosphorylation. In comparison to antibodies disclosed in the prior art which also bind specifically to FcγRIIB, the antibodies according to the present invention surprisingly show a much stronger effect on ITIM phosphorylation which could not have been expected. Such a stronger effect is advantageous. In particular, activation-inhibition coupling, the pairing of a positive signal with an inhibitory loop, controls the magnitude and duration of many biologic processes. In B lymphocytes, recognition of an antigen by the clonotypic B cell receptor (BCR) induces a signal that can direct clonal expansion, differentiation, the release of cytokines, and, ultimately, Ig production. Uncontrolled activation is prevented by exhaustion of the activating stimulus as well as by the triggering of a negative feedback loop that involves the engagement of an inhibitory Fcγ receptor (FcγR), FcγRIIb (CD32B). The latter mechanism is triggered when the BCR recognizes immune-complexed antigen, resulting in the concomitant engagement of CD32B by the Fc domain of the complex-bound IgG, thus preventing the expansion of B cell clones that share the same specificity as that recognized by the soluble IgG. Thus, a successful negative regulatory strategy should form the molecular basis for the negative signaling loop. The antibodies provided by the present invention show a markedly stronger effect on ITIM phosphorylation of CD32B and, thus, they are expected to have a stronger impact on the negative signaling loop triggered by ITIM phosphorylation of CD32B which in turn controls B cells which are involved, inter alia, in autoimmune diseases.

Specifically, antibodies of the present invention preferably increase ITIM phosphorylation of FcγRIIB of Daudi cells in comparison to Daudi cells not treated with said antibody. The increase is preferably 1.5, 2, 3, 4, 5, 6, 7, 8, 9, or 10-fold. From prior art antibodies that bind to CD32B the advantageous properties of the antibodies of the present invention could neither have been expected nor foreseen, let alone would there have been a reasonable expectation of success to provide them, in particular the CDRs or variable heavy and/or light chain as characterized herein. In addition to this improved property of the antibodies of the present invention, the antibodies described herein also having a high specificity for human FcγRIIB and/or are non-blocking, i.e., that their binding to the Fc receptor via their variable region(s) does not interfere with the binding of immune complexes (ICs) or aggregated IgG to the cells.

Accordingly, the present invention provides an anti-FcγRIIB antibody, preferably of an IgG-type, which comprises in its heavy chain variable region H-CDR1, H-CDR2 and H-CDR3 as shown in SEQ ID NOs. 29, 30 and 31 and in its light chain variable region L-CDR1, L-CDR2 and L-CDR3 shown in SEQ ID NOs. 32, 33 and 34. Such an antibody increases ITIM phosphorylation of FcγRIIB of Daudi cells about 4 to 10-fold in comparison to Daudi cells not treated with said antibody.

It is apparent from FIG. 7 that prior art antibodies GB3 (see WO 2005/051999) and 2B6 (see WO 2004/016750) are not able to increase ITIM phosphorylation of FcγRIIB as can be increased by an antibody of the present invention, such as 8A6—either as chimeric or humanized 8A6 antibody. The ability or inability, respectively, to increase ITIM phosphorylation of FcγRIIB seems thus to be dependent on the CDRs, particularly on some key residues which are present in 8A6, but not in GB3 and/or 2B6, respectively. Hence, amino acids that are only present in CDRs of 8A6 at positions that correspond to the respective positions within a CDR of 2B6 or GB3 may be regarded as "key residues".

Visual comparison of the CDRs from 2B6, GB3 and 8A6 for key residues reveals that an antibody of the present invention comprises in H-CDR1 the amino acid sequence shown in SEQ ID NO. 29, in H-CDR2 it comprises the amino acid sequence shown in SEQ ID NO. 30, in H-CDR3 it comprises the amino acid sequence shown in SEQ ID NO. 31, in L-CDR1 it comprises the amino acid sequence shown in SEQ ID NO. 32, in L-CDR2 it comprises the amino acid sequence shown in SEQ ID NO. 33 and in L-CDR3 it comprises the amino acid sequence shown in SEQ ID NO. 34.

The differences between the amino acid sequences of the CDRs of 8A6, GB3 and 2B6 can also be expressed as degree identity (in %-identity) that is allowed in the CDRs of an antibody of the present invention when using the CDRs of 8A6 as reference sequences. Accordingly, an H-CDR1 of an antibody of the present invention is preferably characterized as being 60% or more, such as 70%, 80% or 90% identical to the H-CDR1 as shown in SEQ ID NO. 20.

An H-CDR2 of an antibody of the present invention is preferably characterized as being 36% or more, such as 40%, 50%, 60%, 70%, 80%, or 90% identical to the H-CDR2 as shown in SEQ ID NO. 21.

An H-CDR3 of an antibody of the present invention is preferably characterized as being 50% or more, such as 60%, 70%, 80%, or 90% identical to the H-CDR3 as shown in SEQ ID NO. 22.

An L-CDR1 of an antibody of the present invention is preferably characterized as being 64% or more, such as 70%, 80%, or 90% identical to the L-CDR1 as shown in SEQ ID NO. 23.

An L-CDR2 of an antibody of the present invention is preferably characterized as being 29% or more, such as 30%, 40%, 50%, 60%, 70%, 80%, or 90% identical to the L-CDR2 as shown in SEQ ID NO. 24.

An L-CDR3 of an antibody of the present invention is preferably characterized as being 78% or more, such as 80%, or 90% identical to the L-CDR3 as shown in SEQ ID NO. 25.

Accordingly, the present invention provides an anti-FcγRIIB antibody which comprises in its heavy chain variable region an H-CDR1 sequence which is 60% or more identical to the H-CDR1 sequence shown in SEQ ID NO. 20, an H-CDR2 sequence which is 36% or more identical to the H-CDR2 sequence shown in SEQ ID NO. 21, an H-CDR3 sequence which is 50% or more identical to the H-CDR3 sequence shown in SEQ ID NO. 22, a L-CDR1 sequence which is 64% or more identical to the L-CDR1 sequence shown in SEQ ID NO. 23, a L-CDR2 sequence which is 29% or more identical to the L-CDR2 sequence shown in SEQ ID NO. 24, and a L-CDR3 sequence which is 78% or more identical to the L-CDR3 sequence shown in SEQ ID NO. 25.

Preferably, such an antibody still comprises in its heavy and light chain variable region CDRs the "key residues" as defined in SEQ ID NOs. 29, 30, 31 (H-CDRs) and as defined in SEQ ID NOs. 32, 33 and 34 (L-CDRs).

Such an antibody preferably increases ITIM phosphorylation of FcγRIIB of Daudi cells about 4 to 10-fold in comparison to Daudi cells not treated with said antibody.

As used herein, the term "% identity" refers to the percentage of identical amino acid residues at the corresponding position within the sequence when comparing two amino acid sequences with an optimal sequence alignment as exemplified by the ClustalW or X techniques as available from www.clustal.org, or equivalent techniques. For example, in case of CDR alignments, each of the CDRs (from the heavy and light chain variable region, respectively) shown in SEQ ID NOs. 20-25 serves as reference sequence for a CDR sequence of interest of a heavy or light chain variable region, respectively, e.g. H-CDR1 of SEQ ID NO. 20 is aligned with an H-CDR1 of interest. Accordingly, both sequences (reference sequence and sequence of interest) are aligned, identical amino acid residues between both sequences are identified and the total number of identical amino acids is divided by the total number of amino acids (amino acid length) of SEQ ID NO. 20, 21, 22, 23, 24, or 25, respectively, dependent on whether H-CDR1, H-CDR2, H-CDR3, L-CDR1, L-CDR2, or L-CDR3 are aligned. The result of this division is a percent value, i.e. percent identity value/degree.

The H-CDR1 sequences shown in SEQ ID NOs. 14 and 20 are preferred species sequences of the H-CDR1 shown in SEQ ID NO. 29.

The H-CDR2 sequences shown in SEQ ID NOs. 15 and 21 are preferred species sequences of the H-CDR2 shown in SEQ ID NO. 30.

The H-CDR3 sequences shown in SEQ ID NOs. 16 and 22 are preferred species sequences of the H-CDR3 shown in SEQ ID NO. 31.

The L-CDR1 sequences shown in SEQ ID NOs. 17 and 23 are preferred species sequences of the L-CDR1 shown in SEQ ID NO. 32.

The L-CDR2 sequences shown in SEQ ID NOs. 18 and 24 are preferred species sequences of the L-CDR2 shown in SEQ ID NO. 33.

The L-CDR3 sequences shown in SEQ ID NOs. 19 and 25 are preferred species sequences of the L-CDR3 shown in SEQ ID NO. 34.

Accordingly, the present invention provides an anti-FcγRIIB antibody, preferably of an IgG-type, which
  (a) comprises in its heavy chain variable region H-CDR1, H-CDR2 and H-CDR3 as shown in SEQ ID NOs. 14, 15 and 16 and in its light chain variable region L-CDR1, L-CDR2 and L-CDR3 shown in SEQ ID NOs. 17, 18 and 19; or
  (b) comprises in its heavy chain variable region H-CDR1, H-CDR2 and H-CDR3 as shown in SEQ ID NOs. 20, 21 and 22 and in its light chain variable region L-CDR1, L-CDR2 and L-CDR3 shown in SEQ ID NOs. 23, 24 and 25,
  wherein said antibody preferably increases ITIM phosphorylation of FcγRIIB of Daudi cells about 4 to 10-fold in comparison to Daudi cells not treated with said antibody.

Anti-FcγRIIB antibodies comprising in its heavy chain variable region H-CDR1, H-CDR2 and H-CDR3 as shown in SEQ ID NOs. 14, 15 and 16 and in its light chain variable region L-CDR1, L-CDR2 and L-CDR3 shown in SEQ ID NOs. 17, 18 and 19, or having in its heavy chain variable region H-CDR1, H-CDR2 and H-CDR3 as shown in SEQ ID NOs. 20, 21 and 22 and in its light chain variable region L-CDR1, L-CDR2 and L-CDR3 shown in SEQ ID NOs. 23, 24 and 25 are preferred antibodies. These preferred antibodies preferably increase ITIM phosphorylation of FcγRIIB of Daudi cells about 4 to 10-fold in comparison to Daudi cells not treated with said antibody.

An "antibody" when used herein is a protein comprising one or more polypeptides (comprising one or more binding domains, preferably antigen binding domains) substantially or partially encoded by immunoglobulin genes or fragments of immunoglobulin genes. The term "immunoglobulin" (Ig) is used interchangeably with "antibody" herein. The recognized immunoglobulin genes include the kappa, lambda, alpha, gamma, delta, epsilon and mu constant region genes, as well as myriad immunoglobulin variable region genes. In particular, an "antibody" when used herein, is typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., IgG1, IgG2, IgG3, IgG4, IgA1, and IgA2, with IgG being preferred in the context of the present invention. An antibody of the present invention is also envisaged which has an IgE constant domain or portion thereof that is bound by the Fc epsilon receptor I. An IgM antibody consists of 5 of the basic heterotetramer unit along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each light chain includes an N-terminal variable (V) domain (VL) and a constant (C) domain (CL). Each heavy chain includes an N-terminal V domain (VH), three or four C domains (CHs), and a hinge region.

The constant domains are not involved directly in binding an antibody to an antigen, but can exhibit various effector functions, such as participation of the antibody dependent cellular cytotoxicity (ADCC). If an antibody should exert ADCC, it is preferably of the IgG1 subtype, while the IgG4 subtype would not have the capability to exert ADCC.

When used herein the term "antibody" does not only refer to an immunoglobulin (or intact antibody), but also refers to a fragment thereof, and encompasses any polypeptide comprising an antigen-binding fragment or an antigen-binding domain. Preferably, the fragment such as Fab, F(ab'), F(ab')$_2$, Fv, scFv, Fd, disulfide-linked Fvs (sdFv), and other antibody fragments that retain antigen-binding function as described herein. Typically, such fragments would comprise an antigen-binding domain and have the same properties as the antibodies described herein.

The term "antibody" also includes but is not limited to, but encompasses monoclonal, monospecific, poly- or multi-specific antibodies such as bispecific antibodies, humanized, camelized, human, single-chain, chimeric, synthetic, recombinant, hybrid, mutated, grafted, and in vitro generated antibodies, with chimeric or humanized antibodies being preferred. The term "humanized antibody" is commonly defined for an antibody in which the specificity encoding CDRs of HC and LC have been transferred to an appropriate human variable frameworks ("CDR grafting"). The term "antibody" also includes scFvs, single chain antibodies, diabodies or tetrabodies, domain antibodies (dAbs) and nanobodies. In terms of the present invention, the term "antibody" shall also comprise bi-, tri- or multimeric or bi-, tri- or multifunctional antibodies having several antigen binding sites, preferably at least one of them is a FcγRIIB-specific binding site.

Furthermore, the term "antibody" as employed in the invention also relates to derivatives of the antibodies (including fragments) described herein. A "derivative" of an antibody comprises an amino acid sequence which has been altered by the introduction of amino acid residue substitutions, deletions or additions. Additionally, a derivative encompasses antibodies which have been modified by a covalent attachment of a molecule of any type to the antibody or protein. Examples of such molecules include sugars, PEG, hydroxyl-, ethoxy-, carboxy- or amine-groups but are not limited to these. In effect the covalent modifications of the antibodies lead to the glycosylation, pegylation, acetylation, phosphorylation, amidation, without being limited to these.

The antibody of the present invention is preferably an "isolated" antibody. "Isolated" when used to describe antibodies disclosed herein, means an antibody that has been identified, separated and/or recovered from a component of its production environment. Preferably, the isolated antibody is free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated antibody will be prepared by at least one purification step.

As used herein, the term "specifically binds" refers to antibodies or fragments or derivatives thereof that specifically bind to FcγRIIB or a fragment thereof and do not specifically bind to other Fc receptors. The antibodies or fragments or derivatives thereof according to the invention bind to FcγRIIB through the variable domain of the antibody. However, these antibodies may also be bound by the Fc gamma RIIB through their Fc domain.

The pairing of a VH and VL together forms a single antigen-binding site. The CH domain most proximal to VH is designated as CH1. Each L chain is linked to an H chain by one covalent disulfide bond, while the two H chains are linked to each other by one or more disulfide bonds depending on the H chain isotype. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as H1 or H-CDR1, H2 or H-CDR2 and H3 or H-CDR3, while CDR constituents on the light chain are referred to as L1 or L-CDR1, L2 or L-CDR2, and L3 or L-CDR3.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "complementarity determining regions" (CDRs). The terms "CDR", and its plural "CDRs", refer to a complementarity determining region (CDR) of which three make up the binding character of a light chain variable region (L1-CDRL1, L2-CDR and L3-CDR) and three make up the binding character of a heavy chain variable region (H1-CDR, H2-CDR and H3-CDR). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., loc. cit.; Chothia et al., J. Mol. Biol, 1987, 196: 901; and MacCallum et al, J. Mol. Biol, 1996, 262: 732). However, the numbering in accordance with the so-called Kabat system is preferred.

Preferred variable regions of an antibody of the present invention are shown in SEQ ID Nos. 1, 2, 3, and 4.

The term "framework region" refers to the art-recognized portions of an antibody variable region that exist between the more divergent (i.e., hypervariable) CDRs. Such framework regions are typically referred to as frameworks 1 through 4 (FR1, FR2, FR3, and FR4) and provide a scaffold for the presentation of the six CDRs (three from the heavy chain and three from the light chain) in three dimensional space, to form an antigen-binding surface.

Antibodies (including fragments and derivatives thereof) of the present invention preferably or advantageously increase ITIM phosphorylation of FcγRIIB of Daudi cells about 4 or more-fold, such as about 4-fold or more, about 5-fold or more, about 6-fold or more, about 7-fold or more, about 8-fold or more, about 9-fold or more or about 10-fold (i.e. even nearly 10-fold) in comparison to Daudi cells not treated with said antibody. For that comparison, both an antibody of the present invention is preferably used in an amount within the range of 5 µg/ml to 50 µg/ml, such as 10, 15, 20, or 25 µg/ml.

From the results shown in FIGS. 6, 7 and 8, it is apparent that either the chimeric 8A6 (ch8A6) antibody (comprising rat variable regions and a human constant region) or the humanized 8A6 antibody (hu8A6) markedly increase ITIM phosphorylation in comparison to the prior art antibody GB3. Bearing in mind that the CDRs between the chimeric and humanized 8A6 antibodies are nearly identical, while their framework regions (FRs) are different, and the potency of both antibodies to increase ITIM phosphorylation of FcγRIIBs is nearly the same (see FIG. 8), it is reasonable to conclude that the CDRs are causative for the advantageous property of the antibodies of the present invention to markedly increase ITIM phosphorylation, for example, in comparison to the antibody GB3.

The skilled person is readily in a position to graft the CDRs as described herein for the antibodies of the present invention into an appropriate framework or, vice versa, graft framework regions into an antibody having the CDRs of an antibody of the present invention such that the thus-resulting antibody has the advantageous properties, in particular the property of increasing ITIM phosphorylation of CD32B as described herein.

As mentioned, antibodies of the present invention have preferably or advantageously the property to increase ITIM phosphorylation of FcγRIIB (CD32B) of Daudi cells, for example, in comparison to the prior art antibody GB3 described in WO 2005/051999, which is characterized as having the variable region of the heavy chain shown in SEQ ID NO: 7 of WO 2005/051999 (see SEQ ID NO. 26) and the variable region of the light chain shown in SEQ ID NO: 5 of WO 2005/051999 (see SEQ ID NO. 27).

The increase in ITIM phosphorylation of FcγRIIB (CD32B) of Daudi cells effected by an antibody encompassed by the present invention is preferably about 4-fold or more, about 5-fold or more, about 6-fold or more, about 7-fold or more, about 8-fold or more, about 9-fold or more or about 10-fold (i.e. even nearly 10-fold) in comparison to Daudi cells not treated with said antibody.

ITIM phosphorylation of CD32B (Fc gamma IIB receptor) of Daudi cells is preferably determined as follows:

$3 \times 10^5$ Daudi cells suspended in RPMI 1640 medium supplemented with 1% FBS (fetal bovine serum) are either left untreated (control) or incubated for 25 minutes at 37° C., 5% $CO_2$ with an antibody mix containing anti-IgM (anti-human, mouse) and anti-mouse IgG (rabbit) wherein the antibody mix comprises 2 µg/ml α-hIgM (mAB, clone UHB) and 20 µg/ml α-mIgG. Subsequently the cells are either treated 20 minutes at 37° C., 5% $CO_2$ with an antibody encompassed by the present invention or with an antibody of interest as defined herein below, such as the GB3 antibody of WO 2005/051999, respectively, both antibodies are preferably applied at equal concentration, and optionally with buffer as control (w/o). Cells are harvested after incubation at 4° C., lysed and subjected to Western Blot-analysis, whereby phosphorylation is detected by an (anti-) phosphotyrosine antibody (anti-CD32B (phospho Y292) antibody). The Western Blot is optionally probed with an antibody detecting e.g. β-Actin which serves as loading control for Western Blot-analysis. As an alternative to Daudi cells, PBMCs or Raji cells can be used. Accordingly, in all embodiments which apply Daudi cells when determining ITIM phosphorylation Daudi cells can be replaced by Raji cells or PBMCs.

The phosphotyrosine antibody is preferably coupled to a signal generating group. A signal generating group refers to a composition detectable by spectroscopic, photochemical, biochemical, immunochemical, or chemical means. For example, useful labels include radiolabels such as $^{32}P$, $^{35}S$, or $^{125}I$; fluorescent dyes (for example, Cy-3, Cy-5); chromophores, electron-dense reagents; enzymes that generate a detectable signal (e.g., as commonly used in an ELISA); or spin labels. The label or detectable moiety has or generates a measurable signal, such as a radioactive, chromogenic, or fluorescent signal, that can be used to quantify the amount of bound detectable moiety in a sample.

The signal generating group can be covalently or non-covalently bound to the phosphotyrosine antibody. A signal can be determined by way of the signal provided by the signal generating group of a phosphotyrosine antibody. The signal can be any signal which is detectable by, for example, spectroscopic, photochemical, biochemical, immunochemical, or chemical means.

An increase in ITIM phosphorylation is determined by comparing (i) the signal generated from the signal generating group of the phosphotyrosine antibody bound to the ITIM motif of CD32B of cells that were untreated ("reference value") to (ii) the signal generated from the signal generating group of the phosphotyrosine antibody bound to the ITIM motif of CD32B of cells that were treated with an antibody encompassed by the present invention, whereby if signal (ii) is higher than signal (i) an increase in ITIM phosphorylation of CD32B was effected by an antibody encompassed by the present invention. For that comparison an antibody of the present invention is preferably used in an amount within the range of 5 µg/ml to 50 µg/ml, such as 10, 15, 20, or 25 mg/ml. For example, when comparing the prior art antibody GB3 or any other antibody binding to CD32B (collectively called "antibody of interest"), preferably one that binds the epitope on CD32B as described herein and/or that is non-blocking as described herein with an antibody encompassed by the present invention in order to determine the ability of an antibody of interest and an antibody encompassed by the present invention as to how many-fold each antibody may increase ITIM phosphorylation of CD32B, ITIM phosphorylation is determined as described above for the antibody of interest and an antibody encompassed by the present invention. Namely, a value for the comparison of an antibody of interest with untreated cells and a value for the comparison of an antibody encompassed by the present invention with untreated cells is obtained. These values can be compared to each other in order to determine whether an antibody encompassed by the present invention has the ability to increase ITIM phosphorylation to a higher extent, such as 4 to 10-fold (including 4, 5, 6, 7, 8, 9, 10) than an antibody of interest. For that comparison, an antibody of interest and an antibody of the present invention are preferably used in an amount within the range of 5 µg/ml to 50 µg/ml, such as 10, 15, 20, or 25 µg/ml.

The term "Fc gamma receptor IIB" is used herein interchangeably with "FcgRIIB" or "Fcgamma receptor IIB" or "Fcγ receptor IIB" or "FcγRIIB" and comprises both membranous FcγRIIB and soluble (i.e. the extracellular part of a FcγIIB receptor) FcγRIIB. Said term also includes variants of FcγRIIB such as FcγRIIB1 and FcγRIIB2 which differ from each other in a 19 amino acid sequence insertion in the cytoplasmic domain of FcγRIIB1. Another variant encompassed by said term is FcγRIIB3 which is identical to FcγRIIB2, but lacks information for the putative signal peptidase cleavage site.

Sometimes, FcγRIIB is also referred to herein as "CD32B". Thus this term as well as the other terms used to designate Fc gamma receptor IIB as described above, can be interchangeably used with the term "CD32B". Fc gamma receptor IIB belongs to the immunoglobulin superfamily of proteins and is found on many hematopoietic lineages. As its name indicates, Fc receptor IIB recognizes and binds to the Fc (fragment, crystallizable) part of antibodies, i.e. the fragment that corresponds to the two C-terminal domains of both heavy chains of the antibody and typically interacts with effector molecules and cells. A preferred FcγRIIB is shown in SEQ ID NO. 5. A preferred soluble FcγRIIB is shown in SEQ ID NO. 12.

"Soluble FcγRIIB" is also referred to as "sFcγRIIB". As used herein, the term "soluble Fcγ receptor IIB" and analogous terms refer to the extracellular part of the Fay receptor IIB. Such part can be dissolved in a liquid. In general, soluble forms of any FcγR class, isoform or allele can be identified by a preceding "s", e.g., sCD32 or sFcγRII refers to the soluble Fc gamma RII receptor. Typically, in contrast to membranous (i.e., membrane-bound) FcγR, soluble FcγR do not comprise a transmembrane region or an intracytoplasmatic tail.

Preferably, the FcγRIIB of the invention is of human origin or a human FcγRIIB. The term "of human origin" is to be construed in its broadest sense. In general, it means that a FcγR (or a region or fragment thereof) resembles or is similar to a human FcγR (i.e., the protein found in the human body) in terms of amino acid sequence and/or structure.

Alternatively, the FcγRIIB "of human origin" can be a recombinant FcγRIIB that is obtained by expression of a recombinant nucleic acid in a host cell, e.g. as described by Sondermann and Jacob (1999), Bioll. Chem. 380(6), 717-721. Briefly, a gene of interest is obtained from an organism and introduced into a vector, e.g. a plasmid or a virus, which is then used to transfer the gene into a host cell which expresses the recombinant gene and produces a recombinant protein product. The person skilled in the art will readily know which host cell to select in order to obtain a FcγRIIB that is e.g. suitable for the preparation of a pharmaceutical composition. For example, in some embodiments, an unglycosylated FcγRIIB may be desired. The person skilled in the art may then select a prokaryotic host cell for expression of the FcγRIIB that is devoid of the enzyme machinery necessary for protein glycosylation. In one embodiment the FcγRIIB can be expressed in prokaryotes and subsequently purified and refolded according to the description of WO 00/32767.

In another embodiment FcγRIIB can be easily and unexpensively produced in high purity in eukaryotic expression systems. Useful systems include eukaryotes with a specialized apparatus for the production of extracellular proteins, e.g. B cells. Other possible eukaryotic expression systems include, but are not limited to, CHO or HEK cells. Said soluble FcγRIIB is therefore recombinant, soluble and glycosylated FcγRIIB.

FcγRIIB as referred to herein further encompass FcγRIIB that, in comparison to wild type FcγR, has been modified or altered with regard to the amino acid sequence, and include, e.g., additional glycosylation sites or the like. However, also non-glycosylated forms of FcγRIIB are envisaged and are a preferred embodiment of FcγRIIBs.

As regards the heavy chain variable region of an antibody of the present invention, it is preferred that the heavy chain variable region of an antibody of the present invention comprises the amino acid sequence shown in SEQ ID NO. 3, with at least one of the mutations selected from the group consisting of amino acid Q at position 1 being replaced by E, amino acid V at position 11 being replaced by L, amino acid G at position 42 being replaced by K, amino acid S at position 50 being replaced by V, amino acid Y at position 53 being replaced by S, amino acid K at position 58 being replaced by T, amino acid G at position 61 being replaced by A, amino acid S at position 75 being replaced by T, amino acid K at position 76 being replaced by R, amino acid N at position 77 being replaced by S, and amino acid T at position 78 being replaced by N. Such an antibody is preferably characterized as comprising the heavy chain constant region the amino acid sequence shown in SEQ ID NO. 6 and/or the light chain constant region the amino acid sequence shown in SEQ ID NO. 7.

An antibody of the present invention is preferably characterized as comprising the heavy chain constant region the amino acid sequence shown in SEQ ID NO. 6 and/or the light chain constant region the amino acid sequence shown in SEQ ID NO. 7.

In a preferred antibody of the invention, the constant region of the heavy chain contains an alanine residue at position 297 (N297A) according to the EU protein numbering as described by Edelman et al. 1969 (corresponds to the numbering of the sequence which is represented by SEQ ID NO. 6 as shown in FIG. 2). Antibodies with a heavy chain containing an alanine (Ala, A) residue at position 297 (N297A) are designated herein with the suffix "_N297A", while antibodies having an asparagine (Asn, N) residue at said position are "wildtype" and are thus designated herein with the suffix "(wt)". As can be seen in FIG. 2, the variable region of the heavy chain of the humanized antibody 8A6 wild type ends with an amino acid residue "S" at position 113 according to the EU protein numbering. The constant region of said antibody starts at position 118. The resulting apparent gap of 4 amino acid residues is caused by the switch to the EU protein numbering system for the constant region and does not mean that any amino acid residues are missing.

The antibodies according to the invention having an alanine residue at position 297 of the amino acid sequence represented by SEQ ID NO. 6 do have a reduced or no antibody dependent cellular cytotoxicity due to a reduced or non-existent binding of the Fc part of the antibody to Fc receptors. The amino acid sequence of such a N297A constant region is shown in SEQ ID NO. 28. Accordingly, antibodies of the present invention may contain as constant region the amino acid sequence shown in SEQ ID NO. 28. Such antibodies lack glycosylation at position 297 according to the EU protein numbering. Thus, the present invention encompasses antibodies that lack glycosylation at position 297 according to the EU protein numbering of the heavy chain constant region, but also encompasses antibodies that are glycosylated at position 297 according to the EU protein numbering of the heavy chain constant region.

In a preferred embodiment of the invention, the constant domain (Fc-domain) of the antibody according to the invention has the allotype G1m17 containing the amino-acids K (Lys) at position 214, E (Glu) at position 356, M (Met) at position 358 and A (Ala) at position 431, lacking a C-terminal K (Lys) (Beck et al., 2010).

As used herein, the term "allotype" refers to the human allotype of the antibodies according to the invention. Allotypes are allelic/genetic variants within the constant-region sequences of particular isotypes. The allotypes are inherited in an allelic manner. Different members of a species will therefore differ from one another with respect to which particular alleles of a given isotype they inherited from their parents. Km1 and Km2 are allotypes of humans kappa chains; G1m(4) and G1m(17) are allotypes of human gamma-1 chains.

As regards the light chain variable region of an antibody of the present invention, it is preferred that the light chain variable region of an antibody of the present invention comprises the amino acid sequence shown in SEQ ID NO. 4, with at least one of the mutations selected from the group consisting of amino acid Q at position 1 being replaced by N, amino acid S at position 28 being replaced by N, amino acid S at position 31 being replaced by T, amino acid V at position 33 being replaced by L, amino acid D at position 34 being replaced by A, amino acid Y at position 49 being replaced by F, amino acid T at position 53 being replaced by N, amino acid Y at position 55 being replaced by A, amino acid L at position 89 being replaced by Q, and amino acid N at position 93 being replaced by Y. Such an antibody is preferably characterized as comprising the heavy chain constant region the amino acid sequence shown in SEQ ID NO. 6 and/or the light chain constant region the amino acid sequence shown in SEQ ID NO. 7

In yet another embodiment of the invention, the constant light domain is of the Km3 allotype comprising amino-acids A (Ala) at position 153 and V (Val) at position 191.

An antibody of the present invention preferably comprises the heavy chain variable region shown in SEQ ID NO. 1 or 3 and/or the light chain variable region shown in SEQ ID NO. 2 or 4. Accordingly, an antibody of the present invention preferably comprises the heavy chain variable region shown in SEQ ID NO. 1 and the light chain variable region shown in SEQ ID NO. 2 or it comprises the heavy chain variable region shown in SEQ ID NO. 3 and the light chain variable region shown in SEQ ID NO. 4.

An antibody of the present invention preferably comprises the heavy chain variable region shown in SEQ ID NO. 1, the light chain variable region shown in SEQ ID NO. 2, the heavy chain constant region the amino acid sequence shown in SEQ ID NO. 6 and the light chain constant region the amino acid sequence shown in SEQ ID NO. 7.

Alternatively, an antibody of the present invention preferably comprises the heavy chain variable region shown in SEQ ID NO. 3, the light chain variable region shown in SEQ ID NO. 4, the heavy chain constant region the amino acid sequence shown in SEQ ID NO. 6 and the light chain constant region the amino acid sequence shown in SEQ ID NO. 7.

An antibody of the present invention preferably specifically binds to an epitope within amino acids No. 20-40 of human FcγRIIB according to SEQ ID NO. 5.

As used herein, the term "epitope" refers to a part of a polypeptide or protein which confers immunogenic acitivity in an animal and to which an antibody specifically binds. More preferably, the antibody specifically binds to an epitope comprising the motif GTHSPES in SEQ ID NO. 5. This amino acid motif has been shown to be a very specific epitope of FcγRIIB. Antibodies which bind specifically to this epitope do not bind to human FcγRIIA. Binding of an antibody of the invention to this epitope via its variable region(s) does preferably not interfere with binding of Fc parts of antibodies to the receptor and does not block the normal physiological function of the receptor.

Preferably, the antibody of the present invention binds in vitro human FcγRIIb with an affinity having an off-rate constant of at least $4.9 \times 10^{-4}$ s$^{-1}$. An off-rate constant ($k_{off}$) can be measured by surface plasmon resonance experiments. Especially, antibody binding to sFcγRIIB can be analysed by surface plasmon resonance using a BIAcore T200 biosensor (GE Healthcare/Biacore).

As used herein, the term "affinity" refers to the binding strength between the variable regions of one heavy and one light chain of an antibody or fragment or derivative thereof and their antigen (e.g. the FcγRIIB receptor) and is measured in vitro. Affinity determines the strength of the interaction between an epitope and an antibody's antigen binding site. Affinity can be calculated using the following formula:

$$KA = [AB-AG]/[AB]*[AG] = k_{on}/k_{off}$$

wherein:
KA=affinity constant
[AB]=molar concentration of unoccupied binding sites on the antibody
[AG]=molar concentration of unoccupied binding sites on the antigen
[AB−AG]=molar concentration of the antibody-antigen complex As used herein, the term "avidity" refers to the measurement of the overall strength of an antibody-antigen complex, which in effect depends on the parameters (1) affinity of the antibody for the epitope, (2) valency of the antibody and antigen and (3) the structural arrangement of the interacting parts.

The present invention also provides nucleic acid sequences encoding the antibody described herein. As used herein, the terms "nucleic acids" or "nucleotide sequences" refer to DNA molecules (e.g. cDNA or genomic DNA), RNA (mRNA), combinations thereof or hybrid molecules comprised of DNA and RNA. The nucleic acids can be double- or single-stranded and may contain double- and single-stranded fragments at the same time. Most preferred are double stranded DNA molecules.

According to the present invention, a nucleic acid sequence which codes for an inventive antibody comprises nucleotides which encode at least those parts of the antibody which confer the specific binding properties of the antibody according to the invention.

Preferably the nucleic acid sequence according to the invention encodes the variable regions, preferably at least the CDRs as described herein.

Preferred examples of nucleic acid sequences according to the invention are represented by SEQ ID NOs. 8-11. A person skilled in the art would be aware that these nucleotide sequences can vary depending on the employed methods of expression and systems used therefor.

The present invention furthermore provides a nucleic acid vector comprising at least one of the nucleic acid sequences as described herein that encode an antibody of the present invention. The vector preferably comprises a promoter under the control of which the above nucleic acid sequences are placed. The vector can be prokaryotic or an eukaryotic expression vector, where the recombinant nucleic acid is either expressed alone or in fusion to other peptides or proteins.

The invention also provides a host cell which is transfected with the vector mentioned above. The host cell can be any cell, a prokaryotic cell or a eukaryotic cell and can be used to produce at least parts of an antibody or fragment or derivative thereof according to the present invention.

Also provided by the present invention is a method for the production of an antibody of the invention, comprising culturing a host cell as described herein under conditions which allow expression of the nucleic acid sequence comprised by the nucleic acid vector of the invention and recovering the thus produced antibody.

The antibody or fragment or derivative thereof according to the present invention can advantageously be used in a pharmaceutical composition. Such pharmaceutical composition can be applied for the treatment or prophylaxis of diseases or disorders, preferably autoimmune diseases.

FcγRIIB-specific antibodies according to the invention inhibit the immune response in B-cells, dendritc cells and activated granulocytes (e.g., macrophages) which leads to a reduced production of immune stimulatory mediators and to a reduction in antibody production as well as antigen presentation (e.g., on dendritic cells and macrophages leading to a decrease in T-cell recruitment). Taken together the feedback loop of antibody production and restimulation of the immune system is inhibited.

Importantly, the binding of the anti-FcγRII antibody of the invention to the receptor via its variable regions does not interfere with Fc-fragment binding of ICs or antibodies to the receptor, and in contrast to known blocking antibodies the normal function of the Fc-receptor is maintained.

Therefore, in another aspect the present invention relates to a pharmaceutical composition comprising as an active ingredient an antibody or fragment or derivative thereof according to the invention. Said pharmaceutical composition may comprise at least one pharmaceutically acceptable carrier or adjuvant or excipient.

Antibodies may be provided in pharmaceutically acceptable compositions as known in the art or as listed in a generally recognized pharmacopeia for use in animals, and more particular in humans.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The compositions of the invention can be formulated as neutral or salt forms.

Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The above-mentioned pharmaceutical composition can be used for the treatment or prophylaxis or diagnosis of any disease or disorder, preferably of autoimmune diseases, and most preferably of autoimmune diseases characterized by the production of auto-antibodies.

The dosage amounts and frequencies of administration are encompassed by the terms therapeutically effective and prophylactically effective. The dosage and frequency of administration further will typically vary according to factors specific for each patient depending on the specific therapeutic or prophylactic agents administered, the type of disease, the route of administration, as well as age, body weight, response, and the past medical history of the patient. Suitable regimens can be selected by one skilled in the art. As used herein, the term "therapeutically effective amount" refers to an amount of the therapeutic active component or agent which is sufficient to treat or ameliorate a disease or disorder, to delay the onset of a disease or which provides any therapeutical benefit in the treatment or management of a disease.

For antibodies encompassed by the invention, the dosage administered to a patient is typically 0.0001 mg/kg to 100 mg/kg of the patient's body weight. Preferably the administered dosage is about 15 mg/kg. It is well known that human antibodies have a longer half-life within the human body than antibodies from other species. Therefore, the dosage and frequency of administration of antibodies of the invention or fragments or derivatives thereof may be reduced as compared to normally used dosages of antibodies from other species.

Treatment of a subject with a therapeutically or prophylactically effective amount of antibodies or fragment or derivative thereof of the invention can include a single treatment or, preferably, can include a series of treatments. In a preferred embodiment, a subject can be treated with antibodies or fragments or derivatives thereof of the invention in the range of between about 0.1 to 30 mg/kg body weight, one time per week for between about 1 to 10 weeks, preferably between 2 to 8 weeks, more preferably between about 3 to 7 weeks. The most advantageous form and manner of application can be chosen to best benefit the patient to be treated.

Methods of administering an antibody or fragment or derivative thereof of the present invention include, but are not limited to, parenteral administration (e.g., intradermal, intramuscular, intraperitoneal, intravenous and subcutaneous), epidural, and mucosal (e.g., intranasal and oral routes). In a specific embodiment, the antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent.

As used herein, the term "treating" and "treatment" refers to administering to a subject a therapeutically effective amount of a pharmaceutical composition according to the invention. A "therapeutically effective amount" refers to an amount of the pharmaceutical composition or the antibody which is sufficient to treat or ameliorate a disease or disorder, to delay the onset of a disease or to provide any therapeutical benefit in the treatment or management of a disease.

As used herein, the term "prophylaxis" refers to the use of an agent for the prevention of the onset of a disease or disorder. A "prophylacticly effective amount" defines an amount of the active component or pharmaceutical agent sufficient to prevent the onset or recurrence of a disease.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs.

Moreover, antibodies of the invention can be used for diagnostic purposes to detect, diagnose, or monitor diseases, or disorders, in particular autoimmune diseases. Antibodies or fragments or derivatives thereof according to the invention can be used to assay FcγRIIB levels in a biological sample using classical immunohistological methods as described herein or as known to those of skill in the art (e.g., see Jalkanen et al., 1985, J. Cell. Biol. 101: 976-985; Jalkanen et al., 1987, J. Cell. Biol. 105: 3087-3096). Other antibody-based methods useful for detecting protein gene expression include immunoassays, such as the enzyme linked immunosorbent assay (ELISA) and the radioimmunoassay (RIA).

Therefore, the present invention further relates to a diagnostic composition comprising an antibody of the invention. As used herein, the term "diagnostic" refers to any use of the inventive antibody for diagnosing the presence of a FcγRIIB related auto-immune disease, for example the determination of the amount or degree of the surface expression of endogenous FcγRIIB on cells of an individual or patient. It also refers to the determination of the ratio of activatory FcγRIIs to inhibitory FcγRIIs, e.g. the ratio of expressed FcγRIIA to FcγRIIB.

In a preferred embodiment of the invention the diagnostic composition as described above is for the detection and diagnosis of any disease or disorder, especially autoimmune diseases characterized by the production of auto-antibodies. Exemplary autoimmune diseases include Immune Thrombocytopenia, Systemic Lupus Erythematosus, Pernicious Anemia, Addison's disease, Diabetis type 1, Rheumatoid Arthritis, Sjogren's syndrome, Dermato-myositis, Multiple Sclerosis, Myasthenia gravis, Reiter's syndrome, Graves' disease, Pemphigus vulgaris and bullosus, autoimmune Hepatitis, ulcerative Colitis, cold agglutinin disease, Autoimmune peripheral neuropathy, but are not limited to these.

In a preferred embodiment the antibodies of the invention are used for the diagnosis of an autoimmune disease in a human. For example, the antibodies according to the invention can be used to determine the surface expression of FcγRIIB on the cells of an individual suffering from an auto-immune disease Preferably the expression of FcγRIIB on B cells or Plasma cells is detected using the antibody in a FACS analysis. For this the antibody can be modified by a marker reagent, a fluorescent maker or any other marker known to the person skilled in the art to be able to detect using standard procedures. The antibody according to the invention can also be used as a diagnostic tool in combination with antibodies specific for human FcγRIIA known in the state of the art. Thus the expression of FcγRIIB and FcγRIIB on the cells of an individual suffering from an auto-immune disease or an inflammatory disease can be determined and a ratio can be calculated that is a marker for the disease state or progression of the disease or as a marker for diagnosing the disease.

The present invention further provides a diagnostic kit for the detection of autoimmune diseases comprising an antibody or fragment or derivative thereof according to the invention, and optionally marker reagents, carrier reagents and/or suitable and required receptacles.

Sequences

SEQ ID NO. 1: Amino acid sequence of the heavy chain variable region of the rat antibody 8A6

SEQ ID NO. 2: Amino acid sequence of the light chain variable region of the rat antibody 8A6

SEQ ID NO. 3: Amino acid sequence of the heavy chain variable region of the humanized antibody hu8A6

SEQ ID NO. 4: Amino acid sequence of the light chain variable region of the humanized antibody hu8A6

SEQ ID NO. 5: Amino acid sequence of human FcγRIIB

SEQ ID NO. 6: Amino acid sequence of the heavy chain constant region of the humanized antibody hu8A6_wt SEQ ID NO. 7: Amino acid sequence of the light chain constant region of the humanized antibody hu8A6_wt SEQ ID NO. 8: Nucleic acid sequence encoding the heavy chain variable region of the humanized antibody hu8A6

SEQ ID NO. 9: Nucleic acid sequence encoding the light chain variable region of the humanized antibody hu8A6

SEQ ID NO. 10: Nucleic acid sequence encoding the heavy chain constant region of the humanized antibody hu8A6_wt SEQ ID NO. 11: Nucleic acid sequence encoding the light chain constant region of the humanized antibody hu8A6_wt SEQ ID NO. 12: Amino acid sequence of human soluble FcγRIIA (sFcγRIIA)

SEQ ID NO. 13: Amino acid sequence of mutated human soluble FcγRIIA (sFcγRIIAmut)

SEQ ID NO. 14: Amino acid sequence of CDR1 of the heavy chain variable region of the rat antibody 8A6

SEQ ID NO. 15: Amino acid sequence of CDR2 of the heavy chain variable region of the rat antibody 8A6

SEQ ID NO. 16: Amino acid sequence of CDR3 of the heavy chain variable region of the rat antibody 8A6

SEQ ID NO. 17: Amino acid sequence of CDR1 of the light chain variable region of the rat antibody 8A6

SEQ ID NO. 18: Amino acid sequence of CDR2 of the light chain variable region of the rat antibody 8A6

SEQ ID NO. 19: Amino acid sequence of CDR3 of the light chain variable region of the rat antibody 8A6

SEQ ID NO. 20: Amino acid sequence of CDR1 of the heavy chain variable region of the humanized antibody hu8A6

SEQ ID NO. 21: Amino acid sequence of CDR2 of the heavy chain variable region of the humanized antibody hu8A6

SEQ ID NO. 22: Amino acid sequence of CDR3 of the heavy chain variable region of the humanized antibody hu8A6

SEQ ID NO. 23: Amino acid sequence of CDR1 of the light chain variable region of the humanized antibody hu8A6

SEQ ID NO. 24: Amino acid sequence of CDR2 of the light chain variable region of the humanized antibody hu8A6

SEQ ID NO. 25: Amino acid sequence of CDR3 of the light chain variable region of the humanized antibody hu8A6

SEQ ID NO. 26: Amino acid sequence of the heavy chain variable region of antibody GB3 (see also SEQ ID NO. 7 of WO 2005/051999)

SEQ ID NO. 27 Amino acid sequence of the light chain variable region of antibody GB3 (see also SEQ ID NO. 5 of WO 2005/051999)

SEQ ID NO. 28 Amino acid sequence of a heavy chain constant region containing at position 297 a N to A substitution (assuming that position 1 of the sequence as shown in the sequence listing is position 118)

SEQ ID NO. 29 Amino acid sequence of CDR1 of the heavy chain variable region which comprises key amino acid residues from chimeric and humanized antibody 8A6

SEQ ID NO. 30 Amino acid sequence of CDR2 of the heavy chain variable region which comprises key amino acid residues from chimeric and humanized antibody 8A6

SEQ ID NO. 31 Amino acid sequence of CDR3 of the heavy chain variable region which comprises key amino acid residues from chimeric and humanized antibody 8A6

SEQ ID NO. 32 Amino acid sequence of CDR1 of the light chain variable region which comprises key amino acid residues from chimeric and humanized antibody 8A6

SEQ ID NO. 33 Amino acid sequence of CDR2 of the light chain variable region which comprises key amino acid residues from chimeric and humanized antibody 8A6

SEQ ID NO. 34 Amino acid sequence of CDR3 of the light chain variable region which comprises key amino acid residues from chimeric and humanized antibody 8A6

BRIEF DESCRIPTION OF THE FIGURES

FIG. 1: Surface Plasmon Resonance analysis of humanized 8A6 according to SEQ. ID. No. 3 and 4 in either wildtype or N297A format, ch8A6_N297A (according to SEQ. ID. NO. 14 and 15 and chGB3_N297A.

FIG. 2: Sequences of hu8A6_wt and hu8A6_N297A depicting position of N to A amino acid exchange in N297A format.

FIG. 3: Non-blocking characteristic of ch8A6_N297A. Raji cells were incubated with a set amount of aggregated human IgG and varying amounts of ch8A6_N297A, chGB3_N297A or blocking antibodies 2B6 or R&D Ab. The antibodies according to the invention are non-blocking.

FIG. 4: Binding from 15 µg/ml to 0.005 µg/ml of Protein A purified antibody (hu8A6 VL+hu8A6_VH and ch8A6_N297A) to native FcγRIIB expressed on Raji cells. Humanized 8A6 variants bind with high avidity to FcγRIIB expressed on Raji cells.

FIG. 5: Binding of 15 µg/ml antibody (hu8A6_VH+hu8A6_VL and ch8A6_N297A) to native FcγRIIA expressed on K562 cells. Antibodies according to the invention do not bind to FcγRIIA on K-562.

FIG. 6a: ITIM-Phosphorylation increased by chimeric 8A6 (ch8A6_N297A) in PBMC from healthy donor. PBMC from healthy donor were isolated using Ficoll separation and subsequently left untreated or incubated for 25 minutes with an antibody mix containing anti-IgM (anti-human, mouse) and anti-mouse IgG (rabbit). Subsequently the cells were either treated 20 minutes with 5 µg/mL ch8A6_N297A or buffer as control (w/o). Cells were harvested after incubation and lysed according to protocol. Lysates were subjected to WB-analysis. β-Actin=loading control.

FIG. 6b: Control experiment for ITIM-Phosphorylation. Daudi cells were left untreated or treated for 25 minutes with an isotype control antibody, polyclonal anti-human anti-IgM (polycl. anti-hIgM), monoclonal anti human IgM (anti-hIgM), anti-hIgM+5 µg/mL ch8A6_N297A, anti-mouse IgG from rabbit (α-mouseIgG), α-mouse IgG+5 µg/mL ch8A6_N297A, mix of anti-hIgM and α-mouseIgG (Ab mix) or Ab mix+5 µg/mL ch8A6_N297A). β-Actin=loading control.

FIG. 6c: Antibodies of the present invention enhance ITIM phosphorylation in the presence or absence of cross-linking/colligation of BCR and Fcgamma RIIB in primary PBMCs.

FIG. 7: Comparison of ch8A6_N297A with antibody from the state of the art (chGB3_N297A). Human Daudi cells were incubated for 25 minutes with an antibody mix containing anti-IgM (anti-human, mouse) and anti-mouse IgG (rabbit) or left untreated. Subsequently the cells were either treated 20 minutes with varying amounts of chGB3_N297A or ch8A6_N297A or buffer as control (w/o). Cells were harvested after incubation and lysed according to protocol. Lysates were subjected to WB-analysis. β-Actin=loading control.

FIG. 8: Comparison of the effect of the humanized variant hu8A6_N297A and ch8A6_N297A and chGB3_N297A on ITIM phosphorylation in primary PBMCs. After crosslinking of BCR and FcγRIIB by the antibody mix, the different antibodies were added at 5 µg/ml and Western Blot analysis for ITIM phosphorylation was conducted. β-Actin=loading control.

FIG. 9: Co-Immunoprecipitation of phosphorylated SHIP-1 with FcγRIIB ITIM. After stimulation of Daudi cells with the antibody mix and either ch8A6_N297A, blocking anti-FcγRIIB antibody 2B6 or chGB3_N297A (5 µg/mL), FcγRIIB was precipitated from cell lysates and Western Blot analysis was performed for the phosphatase SHIP-1. Anti-CD32 using pan anti-CD32 antibody (AF1330)=loading control.

FIG. 10: Comparison of humanized 8A6 variants (hu8A6-VH10+VL2/VH10+VL6/VH10+VL7/VH12+VL2/VH12+VL6/VH12+VL7) to ch8A6_N297A. Daudi cells were left incubated for 25 minutes with buffer (untreated) or a mix (antibody mix) containing anti-IgM (anti-human, mouse) and anti-mouse IgG (rabbit). Subsequently the cells were either treated 20 minutes with 0.25 µg/mL of ch8A6_N297A or humanized 8A6 variants (hu8A6-VH10+VL2/VH10+VL6/VH10+VL7/VH12+VL2/VH12+VL6/VH12+VL7). Cells were harvested after incubation and lysed according to protocol. Lysates were subjected to WB-analysis. β-Actin=loading control.

FIG. 11: Comparison of humanized 8A6 variants (hu8A6-VH10+VL2/VH10+VL6/VH10+VL7/VH12+VL2/VH12+VL6/VH12+VL7) to ch8A6_N297A, blocking anti-FcγRIIB and chGB3_N297A. Daudi cells were left incubated for 25 minutes with buffer (untreated) or a mix (antibody mix) containing anti-IgM (anti-human, mouse) and anti-mouse IgG (rabbit). Subsequently the cells were either treated 20 minutes with 0.25 µg/mL of ch8A6_N297A, humanized 8A6 variants (hu8A6-VH10+VL2/VH10+VL6/VH10+VL7/VH12+VL2/VH12+VL6/VH12+VL7), blocking anti-FcγRIIB antibody 2B6 or chGB3_N297A. Cells were harvested after incubation, lysed according to protocol and analyzed in a Western Blot assay. Lysates were subjected to WB-analysis. β-Actin=loading control.

FIG. 12: Experimental setup for SLE-PBL mouse model. PBL from human SLE patients are transfered into immunocompromised mice. PBL cells are engrafted and mice are subsequently treated with control (PBS) or anti-FcγRIIB ch8A6_N297A antibody according to the invention.

EXAMPLES

Preparation of the Monoclonal Antibody 8A6

Figure 13:
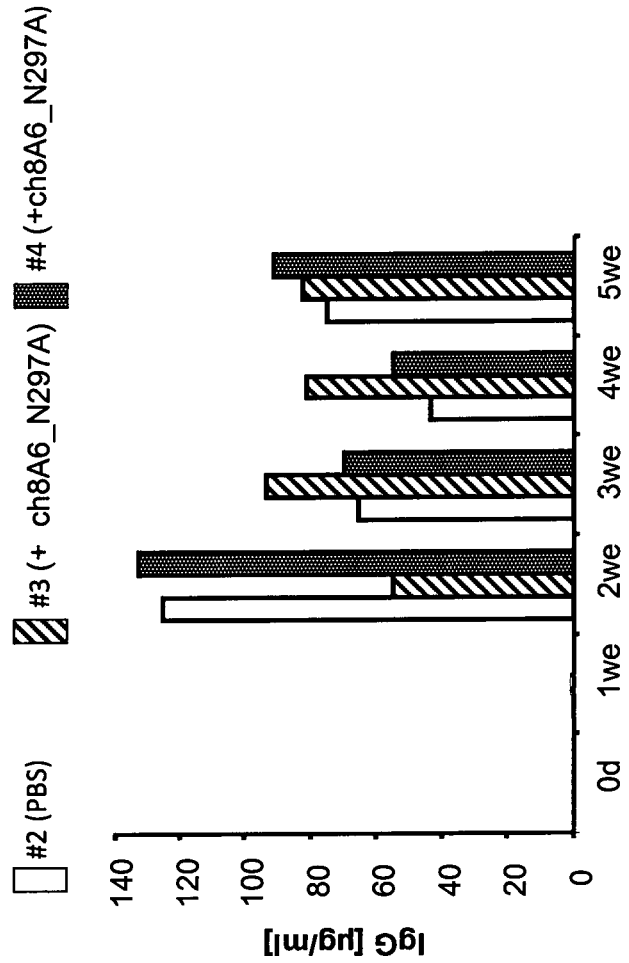
FIG. 13: Total human IgG level [µg/mL] in mice grafted with PBL from human donors suffering from SLE. Depicted are mice treated with control (#2, PBS) or ch8A6_N297A (#3 and #4).

The monoclonal antibody clone 8A6 was produced by immunizing Long-Evans rats with recombinant soluble human FcγRIIB receptor. Hybridoma cell lines from rat spleen cells were produced and screened for antibodies that specifically bind to human FcγRIIB with greater affinity than to FcγRIIA. Secondly the antibodies produced by the aforementioned Hybridomas were screened for non-blocking characteristics, i.e. these antibodies still allow binding of IgG or ICs to membrane-bound FcγRIIB, using techniques known in the art. 50 µg of the purified recombinant soluble human FcγRIIB (sFcγRIIB, SEQ ID NO. 5) were injected intraperitoneally (i.p.) and subcutaneously (s.c.) into LOU/C rats using incomplete Freund's adjuvant supplemented with 5 nmol CpG 2006 (TIB MOLBIOL, Berlin, Germany). After a six weeks interval a final boost with 50 µg sFcγRIIB and CpG 2006 was given i.p. and s.c. three days before fusion. Fusion of the myeloma cell line with the rat immune spleen cells was performed according to standard procedures. Hybridoma supernatants were tested in a solid-phase immunoassay with sFcγRIIB or the irrelevant sFcγRIIA (SEQ ID NO. 12) protein coated to ELISA plates. MAbs from tissue culture supernatant bound to the proteins were detected with HRP conjugated mAbs against the rat IgG isotypes (TIB173 anti-IgG2a, TIB174 anti-IgG2b, TIB170 anti-IgG1 all from ATCC, R-2c anti-IgG2c homemade), thus avoiding mAbs of IgM class. The mAb 8A6 (rat IgG2a) recognized FcγRIIB and did not bind to FcγRIIA using the antigen-specific ELISA assay. A FACS based assay was used to screen the antibodies for specific binding of the native antigen). Additionally the antibodies were screened for non-blocking characteristics, i.e. these antibodies still allow binding of IgG or immune complexes to membrane-bound FcγRIIB.

To produce sufficient amount of antibody for characterization of the chimeric and humanized constructs, FreeStyle™ CHO-S cells were transiently transfected.

The day before transfection cells were seeded at $0.5 \times 10^6$ cells/ml. Cells were centrifuged and resuspended in medium to obtain a final cell concentration of $20 \times 10^6$ cells/ml. For each transfection 3 ml of the cell suspension was transferred to a 6-well plate. The plasmid DNA for transfection was isolated using the HiSpeed Plasmid Maxi Kit (Qiagen) according to the manufacturer's instruction and eluted in endotoxin-free $H_2O$.

For each transfection 75 µg plasmid DNA encoding for the light chain and 75 µg plasmid DNA encoding for the heavy chain were added to the cell suspension and mixed gently. Afterwards PEI (Polyplus) was added and mixed gently. The cells were incubated for 3 h at 37° C. and 5% $CO_2$ under continuous shaking (100 rpm). The cell suspension was filled up with medium to a final volume of 15 ml to achieve a final cell concentration of $4 \times 10^6$ cells/ml and transferred into a 125 ml flask. The cells were incubated at 37° C. and 5% $CO_2$ under continuous shaking (100 rpm) and after 6 d the supernatant was harvested by centrifuging it 2 times (4000 rpm, 5 min). The supernatant was filtered through 0.2 µm filter and antibody titer was determined (see below).

The antibody-titer determination was conducted via two different HPLC methods, Reverse-phase (RP) HPLC and Protein A-HPLC. The RP-HPLC analysis was conducted with an Agilent 1200 Series HPLC system. Data were analyzed with the software "Chem Station for LC Systems" Rev. B.04.02. The solvent components were: Isopropanol (HPLC Grade; Roth), Acetonitril (HPLC Gradient Grade; Roth), H20 (0.2 µm filtered) and Tetrafluoracetat (TFA) (for peptide synthesis; Sigma). Solvent A: H2O, 0.1% TFA; Solvent B: 60% Isopropanol, 30% Acetonitril, 9.9% H2O, and 0.1% TFA. A Phenomenex Jupiter column (#525166-6) with porosity of 300 Å and separation material with a particle diameter of 5 µm was used. Bound antibody was eluted with a linear gradient from 30% to 43% solvent B within 10 min. Detection occurred at λ=210 nm with a UV/VIS detector.

The Protein A-HPLC analysis was conducted with an Agilent 1200 Series HPLC system. Data were analyzed with the software "Chemstation" version Rev. B.04.02. The following solvents were used, solvent A: 0.05M Tris/HCl, 0.1M Glycine, 0.15M NaCl, pH 8.0; solvent B: 0.05M Tris/HCl, 0.1M Glycine, 0.15M NaCl, pH 3.0. For analysis, an Upchurch 2×20 mm analytical guard column was packed with 120 µl of Applied Biosystems Poros® 20A perfusion chromatography media (Life technologies). Bound antibody was eluted with 100% solvent B. In case purified antibody was collected, fractions were neutralized with 56 mM Tris pH 8.0. The expressed antibodies were purified with a 1 ml HiTrap™ rProtein A FF column (GE Healthcare) via fast protein liquid chromatography (Äkta Explorer). The running buffer contained 10 mM Tris-HCl pH 8.0, 150 mM NaCl, the elution buffer was composed of 100 mM glycine, 150 mM NaCl, pH 2.7. Eluted antibodies were neutralized with 60 mM Tris-HCl pH 8.0, concentrated, sterile filtered and stored at −80° C.

Antibody Screening and Characterization of 8A6

Screening of hybridoma supernatants is performed using techniques as known in the state of the art, e.g. ELISA-Binding assay, Biacore assay or FACS-binding analysis. To test antigen specific binding of chimeric 8A6 or the humanized variants, ELISA plates (Nunc-Immuno Plate, F96 Maxisorp) were coated with 1 µg/ml sFcγRIIB, sFcγRIIA (SEQ ID NO. 12) or sFcγRIIAmut (SEQ ID NO. 13) in PBS (100 µl/well) overnight at 4° C. After 3 washing steps in 0.01% Tween in PBS, blocking with 2% BSA in PBS (300 µl/well) was conducted for 2 hours at room temperature. After 3 washing steps, serial dilutions of the purified antibody or supernatant were applied (100 µl/well) and incubated for 1 hour at room temperature. Purified antibodies were diluted in PBS, 2% BSA. Supernatants were supplemented with 10 times PBS and 20% BSA to obtain a final concentration of 2% BSA in PBS. As positive control for FcγRIIA the goat-anti-human FcγRIIA (R&D Systems, AF1875) was used. After 3 washing steps in 0.01% Tween in PBS, the respective secondary antibody donkey-anti-goat-HRP (F(ab')$_2$, Jackson-Immuno-Research) or goat-anti-human-HRP (F(ab')$_2$, Dianova) was incubated for 1 hour at room temperature (100 µl/well). Wells were washed 6 times in 0.01% Tween in PBS. Substrate (OPD containing 0.03% $H_2O_2$) was added (100 µl/well) and the reaction was stopped with 4 M $H_2SO_4$ (50 µl/well). Afterwards the absorbance was measured in a spectrometer at 492 nm.

Analysis of the specific binding to the native antigen of the chimeric 8A6 or humanized variants were conducted via cell binding on Raji (ATCC® CCL-86™) and K-562 cells (ATCC® CCL-243™).

Cells were pelletized by centrifugation (400 g, 5 min) and washed in FACS-buffer (Hanks balanced salt solution, 1% FCS, 0.01% NaN$_3$). After an additional centrifugation step, cells were resuspended in FACS-buffer to obtain a final cell concentration of $2 \times 10^6$ cells/ml and 50 µl of the cell suspension was aliquoted in a 96-well U-bottom plate. Serial dilutions of the humanized variants and ch8A6 were prepared in FACS-buffer.

To verify the expression of FcγRIIA on K-562 cells the mouse-anti-human CD32 antibody (Stem Cell Technologies Inc., Clone VI.3) was diluted in FACS-buffer. 50 µl of the diluted antibodies was added to the cells and incubated for 30 min at 4° C. Cells were washed 2 times in FACS-buffer. Afterwards, 50 µl goat-anti-human IgG-PE conjugated (F(ab')$_2$, Dianova) or goat-anti-mouse IgG-PE conjugated (F(ab')$_2$, Dianova) secondary antibody was diluted in FACS-buffer, added to the cells and incubated for 30 min at 4° C. After 2 washing steps in FACS-buffer, cells were resuspended in 300 µl FACS-buffer and measured in BD FACSCanto™ II (Software: BD FACSDiva™).

To determine whether FcγRIIB antibodies still allow binding of IgG or immune complexes to membrane-bound FcγRIIB a FACS based assay was conducted. Cells were pelletized by centrifugation (400 g, 5 min) and washed in FACS-buffer (Hanks balanced salt solution, 1 FCS, 0.01% NaN$_3$). After an additional centrifugation step, cells were resuspended in FACS-buffer to obtain a final cell concentration of 2×10$^6$ cells/ml. Serial dilutions of the antibodies (ch8A6_N297A, chGB3_N297A, R&D Ab mab1875) were prepared in FACS-buffer. 25 µl of the diluted antibodies were mixed in a 96-well U-bottom plate with 25 µl Alexa488-labeled aggregated Beriglobin (2.5 µl/well). Aggregated human IgG was isolated by size-exclusion chromatography on a Superdex-200 (16/60) from a commercially available pooled IgG product (Beriglobin).

50 µl of the cell suspension was added to the antibody-Beriglobin mixture and incubated for 1 hour at 4° C. Cells were washed 2 times in FACS-buffer. Afterwards, 50 µl goat-anti-human IgG-PE conjugated (F(ab')$_2$, Dianova) or anti-rat-PE secondary antibody was diluted in FACS-buffer, added to the cells and incubated for 30 min at 4° C. After 2 washing steps in FACS-buffer, cells were resuspended in 300 µl FACS-buffer and measured in BD FACSCanto™ II (Software: BD FACSDiva™) (FIG. 3).

FACS Binding Assay

Analysis of the specific binding to the native antigen of the chimeric 8A6 or humanized variants were conducted via cell binding on Raji and K-562 cells.

Cells were pelletized by centrifugation (400 g, 5 min) and washed in FACS-buffer (Hanks balanced salt solution, 1% FCS, 0.01% NaN3). After an additional centrifugation step, cells were resuspended in FACS-buffer to obtain a final cell concentration of 2×106 cells/ml and 50 µl of the cell suspension was aliquoted in a 96-well U-bottom plate. Serial dilutions of the humanized variants and ch8A6 were prepared in FACS-buffer.

Raji and K562 cells were incubated with increasing concentrations of humanized antibodies and the chimeric antibody as control. Raji cells were used to test binding on FcγRIIB (FIG. 4), K562 cells to analyze unspecific binding to FcγRIIA (FIG. 5). Cell bound antibodies were detected with PE-conjugated secondary antibody. All humanized variants bind to FcγRIIB with a comparable affinity as ch8A6_N297A and all humanized variants still bind FcγRIIB with greater avidity than FcγRIIA.

Antibody binding to sFcγRIIB and sFcγRIIA was analysed by surface plasmon resonance using a Biacore T200 biosensor (GE Healthcare/Biacore). Experiments were conducted at LMU, Department of Biology and Microbiology, Service Unit Bioanalytic. Analysed antibodies were captured on a Series S Sensor Chip CM5 sensor chip using the Human Antibody Capture Kit according to the manufacturer's protocol. Hu8A6 variants or ch8A6 were captured at a concentration of 10 nM for 1 min. The analyte sFcγRIIB was injected in various concentrations for 3 min. Measurements were performed at 25° C. and continuous flow (10 µl/min). Data was evaluated using the Biacore T200 Evaluation Software (version 1.0) assuming 1:1 binding.

Chimerization of 8A6 Rat Antibody

The anti-FcγRIIB chimeric monoclonal antibody 8A6 was constructed by fusing the rat 8A6 VH region to a signal peptide and a human IgG1 constant region. Additionally a deglycosylated variant of the heavy chain was generated using an IgG1 constant domain containing a N297A mutation. To construct the 8A6 light chain gene, the rat 8A6 VL region was likewise fused to a signal sequence and the sequence for a human kappa constant region. DNA synthesis of heavy and light chain were performed at Geneart/Life Technologies followed by sub-cloning into a mammalian expression vector.

In Vitro Assays

Cells, Reagents and Antibodies

The human Burkitt lymphoma cell lines Daudi and Ramos were purchased from DSMZ (ACC 78 and ACC 603) and maintained in RPMI 1640 (Gibco/Invitrogen) supplemented with 10% FBS (Gibco/Invitrogen), MEM NEAA (Gibco/Invitrogen), 1 mM sodium pyruvate (Gibco/Invitrogen) and 2 mM L-Glutamine (Gibco/Invitrogen) at 37° C. and 5% CO$_2$. Primary human B cells were purified from heparinized blood of healthy donors using Ficoll density gradients (Leucosep, Greiner Bio-One, Biocoll Separating Solution, Biochrom) and negative magnetic isolation (Dynabeads Untouched Human B Cells, Invitrogen). Purity of the enriched B cells was studied by FACS analysis by staining with anti-hCD19-APC (BD Pharmingen #555415), anti-hCD3-PerCP-Cy5.5 (BD Biosciences #332771) and anti-hCD56-PE (BD Pharmingen #555515). Primary B cells were directly used for the experiments without further culturing. Blocking anti-FcγRIIB antibody 2B6 according to EP1534335.

Stimulation Protocol Using Soluble Antibody Stimulation Mix

For simultaneous stimulation of BCR and FcγRIIB an antibody system was set up using an antibody mix of 2 µg/ml monoclonal mouse anti-hIgM (Southern Biotech #9022-01, clone UHB) and 20 µg/ml monoclonal rabbit anti-mIgG(1, 2a,3) (Epitomics #3020-1, clone M111-2) of which the Fc part cross-reacts with the human FcγRIIB receptor. Controls were conducted with 20 µg/ml polyclonal rabbit anti-hIgM (antibodies online #ABIN117299) or a mix containing 2 µg/ml anti-hIgM and isotype control mIgG2b (clone MPC-11, BD Pharmingen #557351).

3×10$^5$ cells of the lymphoma cell lines Daudi or Ramos and primary B cells were harvested by centrifugation and incubated with the different stimulation mixes in Assay medium (RPMI 1640+1% FBS) for 20 min at 37° C.

Subsequently 5 µg/ml anti-FcγRIIB antibodies ch8A6 (0.8 µl of a 1:10 dilution), 2B6 (1.5 µl of a 1:10 dilution) or chGB3_N297A (1.1 µl of a 1:10 dilution) were added to the samples and cells were further incubated for 25-30 min. Lysis was performed as described separately.

Western Blot Analysis of Phosphorylation Patterns

Cell Lysis

Cells were pelleted at 4° C., washed with ice-cold PBS and incubated in 10 µL lysis buffer (RIPA buffer (Cell Signaling) supplemented with phosphatase inhibitors (PhosStop, Roche), protease inhibitors (Complete Ultra Mini, EDTA-free, Roche) and 1 mM PMSF (Fluka Biochemica) for 30-45 min on ice.

SDS-PAGE

After centrifugation, supernatants were loaded with sample buffer (NuPAGE LDS Sample Buffer, NuPAGE Sample Reducing Agent, Invitrogen) applied to SDS PAGE (NuPAGE Novex Bis-Tris Mini Gels, MES SDS Running Buffer (Invitrogen)). For SDS-PAGE, LDS sample buffer and Reducing Agent were added and samples were heated at 95° C. for 5 min. Samples were stored at −20° C. or directly analyzed by SDS-PAGE and Western Blot.

Protein Transfer to PVDF Membranes and Detection

Subsequently, proteins were transferred to PVDF membranes (Roti-PVDF, Roth, Transfer buffer 10 mM Tris, 100 mM Glycin, 10% Methanol, transfer conditions 240 mA const., 90 min at 4° C.). Membranes were blocked with 5% BSA in TBS-T (10 mM Tris, 150 mM NaCl, 0.1% Tween20) and stained with anti-FcγRIIB/CD32 Phospho (pY292) (Cell Epitomics #2308-1, 1:50000, 4° C. overnight) or anti-phosphoSHIP (1:1000, Cell Signaling #3941) and anti-rabbit-HRP (Jackson ImmunoResearch #111-036-045, 1:50, 000 in TBS-T, 1 h RT). Chemiluminescence (developed with WesternLightning Plus, Perkin Elmer) was detected on X-ray films.

Stripping

For subsequent analyses with antibodies directed against other phosphorylated proteins, membranes were stripped (Re-Blot Plus, Millipore) for 10 min, washed and blocked before staining with anti-β-Actin antibody (Sigma-Aldrich # A1978, 1:50,000 and anti-mouse IgG-HRP, Sigma-Aldrich # A9044) or antibodies for other signaling proteins.

FcγRIIB-ITIM Phosphorylation in PBMC from Healthy Donor Markedly Increased by Inventive Antibodies PBMC from a healthy donor were isolated and either left untreated or incubated for 25 minutes with the stimulation mix (monoclonal mouse anti-hIgM and monoclonal rabbit anti-mIgG). Subsequently, cells were treated either with ch8A6 or buffer as control. Cell lysates were subjected to Western Blot analysis using appropriate detection antibodies as outlined above. A markedly increase in the phosphorylation of the FcγRIIB-IITIM motif of cells (PBMC, B cells) was detected (FIG. 6a). Control experiments with stimulation of cells with stimulation mix alone, or only monoclonal mouse anti-hIgM, monoclonal rabbit anti-mIgG in combination with ch8A6 did not show an increased FcγRIIB-ITIM-phosphorylation (FIG. 6b). The antibodies of the invention thus show a markedly effect on the ITIM-phosphorylation of human cells with crosslinked BCR and membrane-bound (endogenously expressed) FcγRIIB and not on unstimulated cells, i.e. cells without crosslinked BCR and membrane-bound FcγRIIB. During an auto-immune disease, BCR and membrane-bound FcγRIIB will be crosslinked by auto-antigens or immune complexes (ICs). The inventive antibodies are able to inhibit pathogenic autoreactive B cells in an auto-immune disease by increasing FcγRIIB-ITIM-phosphorylation. However, antibodies of the present invention are also able to increase ITIM-phosphorylation without crosslinked BCR (FIG. 6c).

Comparison of the Effects of ch8A6 with Antibody from the State of the Art (chGB3_N297A)

Comparison of the effect of clone ch8A6_N297A and clone chGB3_N297A on ITIM phosphorylation. Human Daudi cells were treated with an antibody mix and, subsequently, ch8A6_N297A, chGB3_N297A or 2B6 as described above. The antibody chGB3_N297A like ch8A6_N297A is a non-blocking anti-FcγRIIB antibody and recognizes a similar epitope.

Addition of ch8A6_N297A to the antibody-mix treated cells showed an increase of FcγRIIB-ITIM phosphorylation already at a concentrations of 0.05 μg/ml. Though increasing concentrations of the chGB3_N297A showed a dose-dependent stimulation of phosphorylation of the inhibitory motif, surprisingly this antibody clone was not able to reach phosphorylation levels comparable to 8A6. Densitometric quantitation of the X-ray film with the software "ImageJ" calculated values of a maximum of 2.8-fold phospho-signals, whereas hu8A6_N297A lead to a 9.8-fold increase compared to untreated cells (FIG. 7). Thus the inventive antibodies clearly and surprisingly show an increased FcγRIIB-ITIM-phosphorylation in comparison to antibodies in the state of the art.

Comparison of the Effect of the Humanized Variant hu8A6, Chimeric 8A6_N297A and chGB3_N297A on ITIM Phosphorylation in Primary PBMC Antibody chGB3_N297A, ch8A6_N297A and humanized 8A6 were compared in their influence on FcγRIIB-ITIM phosphorylation of primary human PBMC. After crosslinking of BCR and FcγRIIB by the antibody mix, the different antibodies were added at 5 μg/ml and Western Blot analysis for ITIM phosphorylation was conducted. Again the inventive antibodies surprisingly have a markedly increased effect on FcγRUB-ITIM-phosphorylation compared to the antibody in the state of the art (FIG. 8).

Co-Immunoprecipitation of the Phosphorylated FcγRIIB-ITIM Motif and SHIP-1

Subsequent to the crosslinking of receptors, the phosphatase SHIP is recruited to the membrane via binding of its SH2 domain to the phospho-tyrosine in the FcγRIIB-ITIM motif, followed by tyrosine phosphorylation at the NPXY motif in the C-terminal domain of SHIP-1. The relocalization in the membrane and subsequent phosphorylation of the NPXY motif is essential for the regulatory function of SHIP-1. Its effect on calcium flux, cell survival, growth, cell cycle arrest and apoptosis is mediated through the PI3K and Akt pathways. Tyr1021 is located in one of the NPXY motifs in SHIP-1, and its phosphorylation is important for SHIP-1 function (Nimmerjahn, Ravetch, 2008).

Human Daudi cells were stimulated with the antibody mix as defined in section above and after lysis in a mild lysis buffer (CoIP lysis buffer), the samples were incubated with 2B6 for capturing FcγRIIB. Complexes were bound to ProteinG-coupled ferromagnetic beads and isolated with a magnetic rack.

Lysates of $1 \times 10^7$ cells/sample were prepared in 500 μl CoIP lysis buffer, incubating the cells for 30 min on ice and vortexing every 10 min. Cell debris was spun down at 13,000 rpm for 10 min at 4° C. and the supernatants were transferred to new tubes. 500 μl of the lysates were incubated with 10 μg 2B6 for 2-3 h at 4° C. end over end. Magnetic Protein G-coupled beads were washed twice with 500 μl lysis buffer and 50 μl beads (1.5 mg) were added to the lysate-antibody-complexes over night at 4° C. (rotating wheel). Complexes were eluted from the beads by washing twice with 200 μl lysis buffer and heating the beads for 5 min in 25 μl 1×LDS sample buffer containing reducing agent. After centrifugation at 4000×g for 30 sec, 10 μl of the supernatant were applied to SDS-PAGE for Western Blot analysis.

Western Blot analyses of the lysates show significantly elevated levels of phospho-SHIP-1 in the samples of cells treated with antibody mix and ch8A6_N297A. As the precipitation was performed with the FcγRIIB-specific antibody 2B6, only isolated SHIP-1 was co-precipitated that had bound to FcγRIIB. Membranes after stripping and restaining showed enhanced phosphorylation of the FcγRIIB-ITIM motif in samples treated with ch8A6_N297A, correlating with the phospho-SHIP1 signals. A second restaining with α-hFcγRIIB a, b, c showed equal amounts of the precipitated receptor FcγRIIB in all samples, serving as a loading control for SDS-PAGE (FIG. 9).

Humanization of ch8A6 ch8A6 was humanized by grafting the complementarity-determining region sequences from the rat antibody onto human frameworks. To select human frameworks the $V_H$ and $V_L$ sequences were compared with those of human Ig variable and joining region germline segments, obtained from publicly available databases (IMGT; V-BASE). VH_3_30 plus IGHJ4 human germline sequences and the VK3_15 plus IGKJ2 human germ-line sequences were chosen for the heavy and light chains, respectively.

Several variants for humanized heavy and light chains were generated. The genes coding for the designed sequences of the humanized $V_H$ and $V_L$ were synthesized at Life Science Technologies/Geneart, followed by sub-cloning into a mammalian expression vector. The screening procedure of the antibody variants were performed directly from the supernatant of transfected CHO-S cells (Invitrogen). The chimeric 8A6 antibody served as a transfection control and standard during the screening of the humanized variants. Hu8A6 variants were analysed for binding on sFcγRIIB and sFcγRIIA via ELISA and on native FcγRIIB via FACS on Raji cells (see above). Additionally a kinetic characterization of the antibody variants was performed with surface plasmon resonance.

Test of Humanized 8A6 Variants

To test the phosphorylation activities of 8A6 humanization variants, Daudi cells were stimulated with the antibody mix, treated with 0.5 or 5 µg/ml of the various 8A6 variants, and Western Blot analysis for ITIM phosphorylation was conducted.

Comparison of Humanized 8A6 Variants to ch8A6_N297A

All tested humanized variants of 8A6 were able to induce phosphorylation of the receptor and phosphorylation levels were comparable to that induced by ch8A6_N297A from the same purification batch. Thus, no loss of activity was detected after the second humanization round. Although Biacore data suggested different affinities for the different combinations of heavy and light chain, those differences were not detectable by Western Blot analyses (FIG. 10)

Comparison of Humanized 8A6 Variants to ch8A6 N297A, Blocking Anti-FcγRIIB (2B6) and chGB3 N297A After the final humanized chain combination was chosen, this variant, combining the heavy chain $V_H10$ with the light chain $V_L6$, was finally compared to the antibodies ch8A6_N297A, 2B6 and chGB3_N297A (FIG. 11).

In Vivo Assays

SLE-PBL-Model

Rag2/gamma-c/Fcγ-/- mice were irradiated at a dosage of 6 Gy and injected intraperitoneally with varying amounts of human peripheral blood leucocytes in 500 µl PBS.

Treatment of mice was started 2 weeks following injection of cells after grafting of human SLE-patient PBL in mice was verified by the presence of human immunoglobulin M or G. Mice were treated with 200 µl buffer (PBS) or 20 µg antibody (ch8A6_N297A) in 200 µl PBS intraperitoneally twice weekly for 4 weeks. Mice were weighed and bled to obtain serum once weekly. Serum samples were frozen at −80° C. until further use (FIG. 12).

ELISA

Serum samples were analyzed by ELISA for the presence of total human IgG, IgM and anti-DNA IgM and IgG.

For quantification of total serum IgM and IgG in serum samples, the Bethyl Human IgM ELISA Quantitation Kit and the Human IgG ELISA Quantitation Kit (Biomol) were used according to the manufacturer's instructions. OD was measured with VersaMax tuneable microplate reader (Molecular Devices) at 450 and 650 nm.

For the detection of anti-DNA antibodies, ELISA plates were coated with 10 µg/mL methylated BSA (Sigma) in PBS for 2 h at room temperature. After washing, the plates were coated with 50 µg/mL calf thymus DNA (Sigma) in PBS at 4° C. overnight. Blocking of unspecific binding was performed with PBS/0.1% Gelatin/3% BSA/1 mM EDTA for 2 h at room temperature. Sera were diluted 1:100 in the blocking solution and incubated for 1 h at room temperature. As a detection antibody, the HRP-conjugated antibody of the human IgM Quantitation Kit (Bethyl) was used and diluted 1:10,000 in blocking solution followed by incubation for 1 h at room temperature. PBS was used for all washing steps. For detection, TMB Solution was added and the reaction was stopped with 6% orthophosphoric acid.

SLE PBL Model, Total Human Serum Immunoglobulin

Total human IgG levels [µg/mL] were analyzed in mice grafted with PBL from human donors suffering from SLE. No significant difference in total human IgG between PBS or anti-FcγRIIB was detected. The antibody according to the invention does not significantly influence total human IgG (FIG. 13).

SLE PBL Model, Influence on Anti-DNA Antibodies (Disease Specific IgG)

Figure 14:
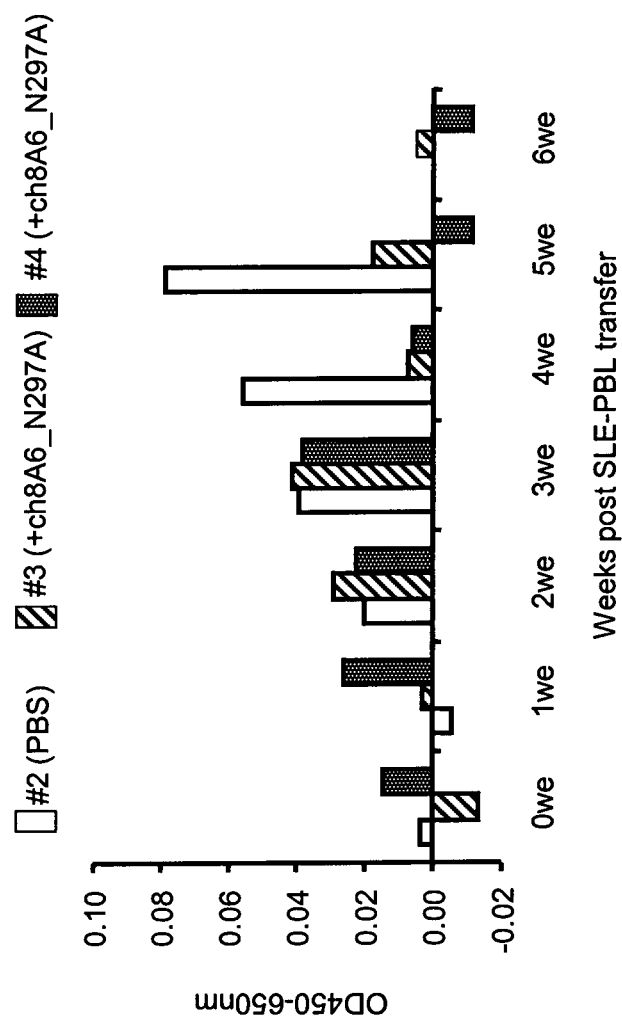
FIG. 14: Reduction in disease specific human anti-DNA IgG in ch8A6_N297A treated mice starting in week 4 post SLE-PBL transfer/grafting using PBL from human donors suffering from SLE. Depicted are anti-DNA IgG titers in two different mice, #3 and #4 (treated with ch8A6_N297A), #2 shows PBS control

A markedly reduction in disease specific human anti-DNA IgG in anti-FcγRIIB mice starting in week 4 post SLE-PBL transfer/grafting was observed. The inventive antibodies specifically reduce the amount of disease relevant anti-DNA antibodies (FIG. 14).

REFERENCES

Almagro J. C. and Fransson J. (2008), Humanization of antibodies. *Front Biosci* 13:1619-33.

Amigorena, S., Bonnerot, C., Drake, J. R., Choquet, D., Hunziker, W., Guillet, J. G., Webster, P., Sautes, C., Mellman, I., Fridman, W. H. (1992), Cytoplasmic domain heterogeneity and functions of IgG Fc receptors in B lymphocytes, Science 256, 1808-1812.

Beck A, Wurch T, Bailly C, Corvaia N. 2010. Strategies and challenges for the next generation of therapeutic antibodies. Nat. Rev. Immunol. 10: 345-352.

Bolland S, Ravetch J V (2000), Spontaneous autoimmune disease in Fc(gamma)RIIB-deficient mice results from strain-specific epistasis. *Immunity* 13(2), 277-85.

Cassel D L, Keller M A, Surrey S, Schwartz E, Schreiber A D, Rappaport E F, McKenzie S E Differential expression of Fc gamma RIIA, Fc gamma RIIB and Fc gamma RIIC in hematopoietic cells: analysis of transcripts. Mol Immunol. 1993 April; 30(5):451-60.

Chan A C and Carter P J. 2010. Therapeutic antibodies for autoimmunity and inflammation Nat. Rev., Immunol. 10(5):301-16.

Daeron M, Latour S, Malbec O, Espinosa E, Pina P, Pasmans S, Fridman W H. 1995. The same tyrosine-based inhibition motif, in the intracytoplasmic domain of Fc gamma RIIB, regulates negatively BCR-, TCR-, and FcR-dependent cell activation. Immunity 3:635-46.

Edelman G M, Cunningham B A, Gall W E, Gottlieb P D, Rutishauser U, Waxdal M J. 1969. The covalent structure of an entire gammaG immunoglobulin molecule. Proc Natl Acad Sci USA. 63(1):78-85.

Ghazizadeh, S., Bolen, J. B. & Fleit, H. B. Physical and functional association of Src-related protein tyrosine kinsases with FcgRII and moncytic THP-1 cells, J. Biol. Chem. 269, 8878-8884 (1994)

Hammerling et al. Monoclonal Antibodies and T-cell Hybridomas, pp. 563-681 (Elsevier, N. Y., 1981)

Harlow et al. ($2^{nd}$ Ed. 1988), Antibodies: A Laboratory Manual, Cold Spring Harbor Laboratory Press.

Isakov N. (1997), ITIMs and ITAMs. The Yin and Yang of antigen and Fc receptor-linked signaling machinery. Immunol Res. 16, 85-100.

Jones, P. T. et al. (1968), Replacing the complementarity-determining regions in a human antibody with those from a mouse, *Nature* 321:522-525.

Malmborg A C, Borrebaeck C A. (1995) BIAcore as a tool in antibody engineering. J Immunol Methods. 1995 Jun. 14; 183(1):7-13.

Nimmerjahn F, Ravetch J V 2008. Fcγ receptors as regulators of immune responses. Nature Reviews Immunology 8, 34-47.

Presta L. G. (2008), Molecular engineering and design of therapeutic antibodies. *Curr Opin Immunol.* 20(4):460-70.

Ravetch, J. V. and Bolland, S. (2001), IgG Fc Receptors. Annu. Rev. Immunol. 19, 275-290.

Reichert J M. (2012) Marketed therapeutic antibodies compendium. MAbs 4(3):413-5

Santos A. D. and Padlan E. A. (1998), Development of more efficacious antibodies for medical therapy and diagnosis. *Prog Nucleic Acid Res Mol Biol.* 60:169-94.

Winter G, Milstein C. (1991) Man-made antibodies. Nature. 349(6307):293-9.

Xiang Z, Cutler A J, Brownlie R J, Fairfax K, Lawlor K E, Severinson E, Walker E U, Manz R A, Tarlinton D M, Smith K G. 2007. FcgammaRIIb controls bone marrow plasma cell persistence and apoptosis. Nat Immunol. 8(4):419-29.

Zhou, M.-J., Todd, R. F., van de Winkel, J. G. J., Petty, H. R. (1993), Cocapping of the leukoadhesin molecules complement receptor type 3 and lymphocyte function-associated antigen-1 with FcγRIII on human neutrophils. Possible role of lectin-like interactions, J. Immunol. 150, 3030-3041.

The invention claimed is:

1. An anti-FcγRIIB antibody which:
   (a) comprises in its heavy chain variable region H-CDR1, H-CDR2 and H-CDR3 as shown in SEQ ID NOs. 14, 15 and 16 and in its light chain variable region L-CDR1, L-CDR2 and L-CDR3 shown in SEQ ID NOs. 17, 18 and 19; or
   (b) comprises in its heavy chain variable region H-CDR1, H-CDR2 and H-CDR3 as shown in SEQ ID NOs. 20, 21 and 22 and in its light chain variable region L-CDR1, L-CDR2 and L-CDR3 shown in SEQ ID NOs. 23, 24 and 25;
   wherein said antibody increases ITIM phosphorylation of FcγRIIB of Daudi cells about 4 to 10-fold in comparison to Daudi cells not treated with said antibody.

2. The antibody of claim 1, wherein said antibody is chimeric or humanized.

3. The antibody of claim 1, comprising in its heavy chain variable region H-CDR1, H-CDR2 and H-CDR3 as shown in SEQ ID NOs. 20, 21 and 22 and in its light chain variable region L-CDR1, L-CDR2 and L-CDR3 shown in SEQ ID NOs. 23, 24 and 25, wherein said antibody comprises the heavy chain variable region shown in SEQ ID NO. 3.

4. The antibody of claim 1, wherein said antibody specifically binds to amino acids No. 20-40 of human FcγRIIB according to SEQ ID NO. 5.

5. The antibody of claim 1, wherein said antibody in vitro binds to human FcγRIIb with an affinity having an off-rate constant of at least $4.9 \times 10^{-4}$ s$^{-1}$.

6. The antibody according to claim 1, wherein said antibody comprises in its heavy chain constant region the amino acid sequence shown in SEQ ID NO. 6.

7. The antibody according to claim 1, wherein said antibody comprises in its light chain constant region the amino acid sequence shown in SEQ ID NO. 7.

8. An anti-FcγRIIB antibody wherein said antibody comprises the heavy chain variable region shown in SEQ ID NO. 1 or 3 and/or the light chain variable region shown in SEQ ID NO. 2 or 4.

9. The antibody of claim 8, wherein said antibody comprises in its heavy chain constant region the amino acid sequence shown in SEQ ID NO. 6.

10. The antibody of claim 8, wherein said antibody comprises in its light chain constant region the amino acid sequence shown in SEQ ID NO. 7.

11. A pharmaceutical composition comprising as an active ingredient an antibody of claim 1.

12. A method of treating an autoimmune disease, the autoimmune disease being characterized by the production of auto-antibodies, comprising administering the antibody of claim 1 to a subject in need thereof, wherein the autoimmune disease is Immune Thrombocytopenia, Systemic Lupus Erythematosus, Pernicious Anemia, Addison's disease, Diabetes type 1, Rheumatoid Arthritis, Sjogren's syndrome, Dermato-myositis, Multiple Sclerosis, Myasthenia gravis, Reiter's syndrome, Graves disease, Pemphigus vulgaris and bullosus, autoimmune Hepatitis, ulcerative Colitis, cold agglutinin disease, and Autoimmune peripheral neuropathy.

* * * * *

SEQUENCE LISTING

```
<160> NUMBER OF SEQ ID NOS: 34

<210> SEQ ID NO 1
<211> LENGTH: 113
<212> TYPE: PRT
<213> ORGANISM: Rattus norvegicus
<220> FEATURE:
<221> NAME/KEY: MISC_FEATURE
<222> LOCATION: (1)..(113)
<223> OTHER INFORMATION: VH r8A6

<400> SEQUENCE: 1

Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Lys Lys Gly Leu Glu Trp Val
        35                  40                  45

Ala Ser Ile Ser Ser Asp Gly Ser Asn Thr Tyr Tyr Gly Asp Ser Val
    50                  55                  60

Lys Gly Arg Phe Thr Ile Ser Arg Asp Asn Thr Arg Ser Asn Leu Tyr
65                  70                  75                  80

Leu Gln Met Asn Ser Leu Arg Ser Glu Asp Thr Ala Thr Tyr Tyr Cys
                85                  90                  95

Ala Arg Pro Gly Asp Tyr Trp Gly Gln Gly Val Met Val Thr Val Ser
            100                 105                 110

Ser

<210> SEQ ID NO 2
<211> LENGTH: 108
<212> TYPE: PRT
<213> ORGANISM: Rattus norvegicus
<220> FEATURE:
<221> NAME/KEY: MISC_FEATURE
<223> OTHER INFORMATION: VL r8A6
<220> FEATURE:
<221> NAME/KEY: MISC_FEATURE
<222> LOCATION: (1)..(108)
<223> OTHER INFORMATION: VL r8A6

<400> SEQUENCE: 2

Asn Ile Val Met Thr Gln Ser Pro Thr Ser Met Phe Ile Ser Val Gly
1               5                   10                  15

Asp Arg Val Thr Met Asn Cys Lys Ala Ser Gln Asn Val Gly Thr Tyr
            20                  25                  30
```

Val Asp Trp Phe Gln Gln Lys Thr Gly Gln Ser Pro Thr Leu Leu Ile
              35                  40                  45

Phe Gly Ala Ser Asn Arg Tyr Thr Gly Val Pro Asp Arg Phe Thr Gly
      50                  55                  60

Ser Gly Ser Gly Thr Asp Phe Thr Leu Ser Ile Ser Asn Met Gln Ala
65                  70                  75                  80

Glu Asp Leu Ala Val Tyr Tyr Cys Leu Gln Tyr Asn Tyr His Pro Tyr
                  85                  90                  95

Thr Phe Gly Pro Gly Thr Thr Leu Glu Leu Lys Arg
              100                 105

<210> SEQ ID NO 3
<211> LENGTH: 113
<212> TYPE: PRT
<213> ORGANISM: Artificial
<220> FEATURE:
<223> OTHER INFORMATION: humanized antibody
<220> FEATURE:
<221> NAME/KEY: MISC_FEATURE
<222> LOCATION: (1)..(113)
<223> OTHER INFORMATION: VH hu8A6

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
              20                  25                  30

Tyr Met Ala Trp Val Arg Gln Ala Pro Gly Lys Gly Leu Glu Trp Val
              35                  40                  45

Ala Ser Ile Ser Tyr Asp Gly Ser Asn Lys Tyr Tyr Gly Asp Ser Val
      50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                  85                  90                  95

Ala Arg Pro Gly Asp Tyr Trp Gly Gln Gly Thr Leu Val Thr Val Ser
              100                 105                 110

Ser

<210> SEQ ID NO 4
<211> LENGTH: 108
<212> TYPE: PRT
<213> ORGANISM: Artificial
<220> FEATURE:
<223> OTHER INFORMATION: humanized antibody
<220> FEATURE:
<221> NAME/KEY: MISC_FEATURE
<222> LOCATION: (1)..(108)
<223> OTHER INFORMATION: VL hu8A6

<400> SEQUENCE: 4

Gln Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Tyr
              20                  25                  30

Val Asp Trp Tyr Gln Gln Lys Pro Gly Gln Ala Pro Arg Leu Leu Ile
              35                  40                  45

Tyr Gly Ala Ser Thr Arg Tyr Thr Gly Ile Pro Ala Arg Phe Ser Gly
      50                  55                  60

Ser Gly Ser Gly Thr Glu Phe Thr Leu Thr Ile Ser Ser Leu Gln Ser

-continued

```
                65                  70                  75                  80
Glu Asp Phe Ala Val Tyr Tyr Cys Leu Gln Tyr Asn Asn His Pro Tyr
                        85                  90                  95
Thr Phe Gly Gln Gly Thr Lys Leu Glu Ile Lys Arg
                100                 105

<210> SEQ ID NO 5
<211> LENGTH: 181
<212> TYPE: PRT
<213> ORGANISM: Homo sapiens
<220> FEATURE:
<221> NAME/KEY: MISC_FEATURE
<222> LOCATION: (1)..(181)
<223> OTHER INFORMATION: human FcγRIIB

<400> SEQUENCE: 5

Met Gly Thr Pro Ala Ala Pro Pro Lys Ala Val Leu Lys Leu Glu Pro
1               5                   10                  15

Gln Trp Ile Asn Val Leu Gln Glu Asp Ser Val Thr Leu Thr Cys Arg
                20                  25                  30

Gly Thr His Ser Pro Glu Ser Asp Ser Ile Gln Trp Phe His Asn Gly
            35                  40                  45

Asn Leu Ile Pro Thr His Thr Gln Pro Ser Tyr Arg Phe Lys Ala Asn
    50                  55                  60

Asn Asn Asp Ser Gly Glu Tyr Thr Cys Gln Thr Gly Gln Thr Ser Leu
65                  70                  75                  80

Ser Asp Pro Val His Leu Thr Val Leu Ser Glu Trp Leu Val Leu Gln
                    85                  90                  95

Thr Pro His Leu Glu Phe Gln Glu Gly Glu Thr Ile Val Leu Arg Cys
                100                 105                 110

His Ser Trp Lys Asp Lys Pro Leu Val Lys Val Thr Phe Phe Gln Asn
            115                 120                 125

Gly Lys Ser Lys Lys Phe Ser Arg Ser Asp Pro Asn Phe Ser Ile Pro
        130                 135                 140

Gln Ala Asn His Ser His Ser Gly Asp Tyr His Cys Thr Gly Asn Ile
145                 150                 155                 160

Gly Tyr Thr Leu Tyr Ser Ser Lys Pro Val Thr Ile Thr Val Gln Ala
                165                 170                 175

Pro Ser Ser Pro
            180

<210> SEQ ID NO 6
<211> LENGTH: 329
<212> TYPE: PRT
<213> ORGANISM: Artificial
<220> FEATURE:
<223> OTHER INFORMATION: humanized antibody
<220> FEATURE:
<221> NAME/KEY: MISC_FEATURE
<222> LOCATION: (1)..(329)
<223> OTHER INFORMATION: CH hu8A6_wt

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 7
<211> LENGTH: 106
<212> TYPE: PRT
<213> ORGANISM: Artificial
<220> FEATURE:
<223> OTHER INFORMATION: humanized antibody
<220> FEATURE:
<221> NAME/KEY: MISC_FEATURE
<222> LOCATION: (1)..(106)
<223> OTHER INFORMATION: CL hu8A6_wt

<400> SEQUENCE: 7

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
 50                  55                  60
```

```
Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105
```

```
<210> SEQ ID NO 8
<211> LENGTH: 339
<212> TYPE: DNA
<213> ORGANISM: Artificial
<220> FEATURE:
<223> OTHER INFORMATION: humanized antibody
<220> FEATURE:
<221> NAME/KEY: misc_feature
<222> LOCATION: (1)..(339)
<223> OTHER INFORMATION: VH hu8A6

<400> SEQUENCE: 8
caggtgcagc tggtggagtc tgggggaggc gtggtccagc ctggaggtc cctgagactc        60 tcctgtgcag cctctggatt caccttcagt gactattaca tggcctgggt ccgccaggct      120
ccaggcaagg ggctggagtg ggtggcatcc atatcatacg atggaagcaa taagtactac      180
ggagactccg tgaagggccg attcaccatc tccagagaca attccaagaa cacgctgtat      240
ctgcaaatga acagcctgag agctgaggac acggctgtgt attactgtgc gagaccggga      300
gactactggg gccaaggaac cctggtcacc gtcagctca                             339
```

```
<210> SEQ ID NO 9
<211> LENGTH: 324
<212> TYPE: DNA
<213> ORGANISM: Artificial
<220> FEATURE:
<223> OTHER INFORMATION: humanized antibody
<220> FEATURE:
<221> NAME/KEY: misc_feature
<222> LOCATION: (1)..(324)
<223> OTHER INFORMATION: VL hu8A6

<400> SEQUENCE: 9
cagatagtga tgacgcagtc tccagccacc ctgtctgtgt ctccagggga aagagccacc       60
ctctcctgca gggccagtca gtccgttggc tcctatgtcg actggtacca gcagaaacct     120
ggccaggctc ccaggctcct catctatggt gcatccacca ggtacactgg tatcccagcc     180
aggttcagtg gcagtgggtc tgggacagag ttcactctca ccatcagcag cctgcagtct     240
gaagattttg cagtttatta ctgtctgcag tataacaacc atccttacac ttttggccag     300
gggaccaagc tggagatcaa acgt                                            324
```

```
<210> SEQ ID NO 10
<211> LENGTH: 990
<212> TYPE: DNA
<213> ORGANISM: Artificial
<220> FEATURE:
<223> OTHER INFORMATION: humanized antibody
<220> FEATURE:
<221> NAME/KEY: misc_feature
<222> LOCATION: (1)..(990)
<223> OTHER INFORMATION: CH hu8A6_wt

<400> SEQUENCE: 10
gcctccacca agggcccatc ggtcttcccc ctggcaccct cctccaagag cacctctggg       60
ggcacagcgg ccctgggctg cctggtcaag gactacttcc ccgaaccggt gacggtgtcg     120
```

```
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa ggttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggttaa                                     990
```

<210> SEQ ID NO 11
<211> LENGTH: 321
<212> TYPE: DNA
<213> ORGANISM: Artificial
<220> FEATURE:
<223> OTHER INFORMATION: humanized antibody
<220> FEATURE:
<221> NAME/KEY: misc_feature
<222> LOCATION: (1)..(321)
<223> OTHER INFORMATION: CL hu8A6_wt

<400> SEQUENCE: 11

```
acggtggctg caccatcggt cttcatcttc ccgccatctg atgagcagtt gaaatctgga     60
actgcctctg ttgtgtgcct gctgaataac ttctatccca gagaggccaa agtacagtgg    120
aaggtggata acgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gctcgcccgt cacaaagagc    300
ttcaacaggg gagagtgtta g                                              321
```

<210> SEQ ID NO 12
<211> LENGTH: 125
<212> TYPE: PRT
<213> ORGANISM: Homo sapiens
<220> FEATURE:
<221> NAME/KEY: MISC_FEATURE
<222> LOCATION: (1)..(125)
<223> OTHER INFORMATION: hu soluble FCyRIIA

<400> SEQUENCE: 12

Arg Phe Lys Ala Asn Asn Asn Asp Ser Gly Glu Tyr Thr Cys Gln Thr
1               5                   10                  15

Gly Gln Thr Ser Leu Ser Asp Pro Val His Leu Thr Val Leu Ser Glu
            20                  25                  30

Trp Leu Val Leu Gln Thr Pro His Leu Glu Phe Gln Glu Gly Glu Thr
        35                  40                  45

Ile Met Leu Arg Cys His Ser Trp Lys Asp Lys Pro Leu Val Lys Val

```
                        50                  55                  60
Thr Phe Phe Gln Asn Gly Lys Ser Gln Lys Phe Ser Arg Leu Asp Pro
 65                  70                  75                  80

Thr Phe Ser Ile Pro Gln Ala Asn His Ser His Ser Gly Asp Tyr His
                 85                  90                  95

Cys Thr Gly Asn Ile Gly Tyr Thr Leu Phe Ser Ser Lys Pro Val Thr
                100                 105                 110

Ile Thr Val Gln Val Pro Ser Met Gly Ser Ser Ser Pro
                115                 120                 125

<210> SEQ ID NO 13
<211> LENGTH: 179
<212> TYPE: PRT
<213> ORGANISM: Homo sapiens
<220> FEATURE:
<221> NAME/KEY: MISC_FEATURE
<222> LOCATION: (1)..(179)
<223> OTHER INFORMATION: soluble mutated human FCyRIIA

<400> SEQUENCE: 13

Met Ala Pro Pro Lys Ala Val Leu Lys Leu Glu Pro Pro Trp Ile Asn
  1               5                  10                  15

Val Leu Gln Glu Asp Ser Val Thr Leu Thr Cys Gln Gly Ala Arg Ser
                 20                  25                  30

Pro Glu Ser Asp Ser Ile Gln Trp Phe His Asn Gly Asn Leu Ile Pro
                 35                  40                  45

Thr His Thr Gln Pro Ser Tyr Arg Phe Lys Ala Asn Asn Asn Asp Ser
 50                  55                  60

Gly Glu Tyr Thr Cys Gln Thr Gly Gln Thr Ser Leu Ser Asp Pro Val
 65                  70                  75                  80

His Leu Thr Val Leu Ser Glu Trp Leu Val Leu Gln Thr Pro His Leu
                 85                  90                  95

Glu Phe Gln Glu Gly Glu Thr Ile Met Leu Arg Cys His Ser Trp Lys
                100                 105                 110

Asp Lys Pro Leu Val Lys Val Thr Phe Phe Gln Asn Gly Lys Ser Lys
                115                 120                 125

Lys Phe Ser Arg Ser Asp Pro Asn Phe Ser Ile Pro Gln Ala Asn His
130                 135                 140

Ser His Ser Gly Asp Tyr His Cys Thr Gly Asn Ile Gly Tyr Thr Leu
145                 150                 155                 160

Phe Ser Ser Lys Pro Val Thr Ile Thr Val Gln Val Pro Ser Met Gly
                165                 170                 175

Ser Ser Pro

<210> SEQ ID NO 14
<211> LENGTH: 5
<212> TYPE: PRT
<213> ORGANISM: artificial
<220> FEATURE:
<223> OTHER INFORMATION: heavy chain CDR1 from rat antibody 8A6

<400> SEQUENCE: 14

Asp Tyr Tyr Met Ala
  1               5

<210> SEQ ID NO 15
<211> LENGTH: 17
<212> TYPE: PRT
<213> ORGANISM: artificial
```

```
<220> FEATURE:
<223> OTHER INFORMATION: heavy chain CDR2 from rat antibody 8A6

<400> SEQUENCE: 15

Ser Ile Ser Ser Asp Gly Ser Asn Thr Tyr Tyr Gly Asp Ser Val Lys
1               5                   10                  15
Gly

<210> SEQ ID NO 16
<211> LENGTH: 6
<212> TYPE: PRT
<213> ORGANISM: artificial
<220> FEATURE:
<223> OTHER INFORMATION: heavy chain CDR3 from rat antibody 8A6

<400> SEQUENCE: 16

Ala Arg Pro Gly Asp Tyr
1               5

<210> SEQ ID NO 17
<211> LENGTH: 11
<212> TYPE: PRT
<213> ORGANISM: artificial
<220> FEATURE:
<223> OTHER INFORMATION: light chain CDR1 from rat antibody 8A6

<400> SEQUENCE: 17

Lys Ala Ser Gln Asn Val Gly Thr Tyr Val Asp
1               5                   10

<210> SEQ ID NO 18
<211> LENGTH: 7
<212> TYPE: PRT
<213> ORGANISM: artificial
<220> FEATURE:
<223> OTHER INFORMATION: light chain CDR2 from rat antibody 8A6

<400> SEQUENCE: 18

Gly Ala Ser Asn Arg Tyr Thr
1               5

<210> SEQ ID NO 19
<211> LENGTH: 9
<212> TYPE: PRT
<213> ORGANISM: artificial
<220> FEATURE:
<223> OTHER INFORMATION: light chain CDR3 from rat antibody 8A6

<400> SEQUENCE: 19

Leu Gln Tyr Asn Tyr His Pro Tyr Thr
1               5

<210> SEQ ID NO 20
<211> LENGTH: 5
<212> TYPE: PRT
<213> ORGANISM: artificial
<220> FEATURE:
<223> OTHER INFORMATION: heavy chain CDR1 from humanized antibody 8A6

<400> SEQUENCE: 20

Asp Tyr Tyr Met Ala
1               5

<210> SEQ ID NO 21
<211> LENGTH: 17
<212> TYPE: PRT
```

<213> ORGANISM: artificial
<220> FEATURE:
<223> OTHER INFORMATION: heavy chain CDR2 from humanized antibody 8A6

<400> SEQUENCE: 21

Ser Ile Ser Tyr Asp Gly Ser Asn Lys Tyr Tyr Gly Asp Ser Val Lys
1               5                   10                  15

Gly

<210> SEQ ID NO 22
<211> LENGTH: 6
<212> TYPE: PRT
<213> ORGANISM: artificial
<220> FEATURE:
<223> OTHER INFORMATION: heavy chain CDR3 from humanized antibody 8A6

<400> SEQUENCE: 22

Ala Arg Pro Gly Asp Tyr
1               5

<210> SEQ ID NO 23
<211> LENGTH: 11
<212> TYPE: PRT
<213> ORGANISM: artificial
<220> FEATURE:
<223> OTHER INFORMATION: light chain CDR1 from humanized antibody 8A6

<400> SEQUENCE: 23

Arg Ala Ser Gln Ser Val Gly Ser Tyr Val Asp
1               5                   10

<210> SEQ ID NO 24
<211> LENGTH: 7
<212> TYPE: PRT
<213> ORGANISM: artificial
<220> FEATURE:
<223> OTHER INFORMATION: light chain CDR2 from humanized antibody 8A6

<400> SEQUENCE: 24

Gly Ala Ser Thr Arg Tyr Thr
1               5

<210> SEQ ID NO 25
<211> LENGTH: 9
<212> TYPE: PRT
<213> ORGANISM: artificial
<220> FEATURE:
<223> OTHER INFORMATION: light chain CDR3 from humanized antibody 8A6

<400> SEQUENCE: 25

Leu Gln Tyr Asn Asn His Pro Tyr Thr
1               5

<210> SEQ ID NO 26
<211> LENGTH: 104
<212> TYPE: PRT
<213> ORGANISM: artificial
<220> FEATURE:
<223> OTHER INFORMATION: variable region of the heavy chain of antibody
      GB3

<400> SEQUENCE: 26

Val Gln Leu Gln Gln Ser Gly Pro Glu Leu Val Lys Pro Gly Ala Ser
1               5                   10                  15

Val Lys Ile Ser Cys Lys Ala Ser Gly Tyr Thr Phe Thr Asp Tyr Tyr
                20                  25                  30

```
Ile Tyr Trp Val Lys Gln Trp Pro Gly Gln Gly Leu Glu Trp Ile Gly
        35                  40                  45

Trp Ile Phe Pro Gly Thr Gly Asn Thr Tyr Tyr Asn Glu Asn Phe Lys
        50                  55                  60

Asp Lys Ala Thr Leu Thr Ile Asp Arg Ser Ser Ser Thr Ala Tyr Met
65                  70                  75                  80

Leu Leu Gly Ser Leu Thr Ser Glu Asp Ser Ala Val Tyr Phe Cys Tyr
                85                  90                  95

Gly Pro Phe Ala Tyr Trp Gly Gln
            100
```

<210> SEQ ID NO 27
<211> LENGTH: 104
<212> TYPE: PRT
<213> ORGANISM: artificial
<220> FEATURE:
<223> OTHER INFORMATION: variable region of the heavy chain of the
      antibody GB3

<400> SEQUENCE: 27

```
Arg Ile Gln Leu Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
                20                  25                  30

Leu Ser Trp Leu Gln Gln Lys Pro Asp Gly Thr Ile Lys Arg Leu Ile
        35                  40                  45

Tyr Ala Thr Ser Ala Leu Asp Ser Gly Val Pro Lys Arg Phe Ser Gly
        50                  55                  60

Ser Gly Ser Gly Ser Asn Tyr Ser Leu Thr Ile Ser Ser Leu Glu Ser
65                  70                  75                  80

Glu Asp Phe Ala Asp Tyr Tyr Cys Leu Gln Tyr Ala Asn Tyr Pro Tyr
                85                  90                  95

Thr Phe Gly Gly Gly Thr Lys Leu
            100
```

<210> SEQ ID NO 28
<211> LENGTH: 329
<212> TYPE: PRT
<213> ORGANISM: artificial
<220> FEATURE:
<223> OTHER INFORMATION: IgG heavy chain constant region with N to A
      change at position 297 when regarding pos. 1 as pos. 118

<400> SEQUENCE: 28

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
                Pro Ala Pro Glu Leu Leu Gly Gly Pro Ser Val Phe Leu Phe Pro Pro
                        115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
                145                 150                 155                 160

Tyr Val Asp Gly Val Glu Val His Asn Ala Lys Thr Lys Pro Arg Glu
                                165                 170                 175

Glu Gln Tyr Ala Ser Thr Tyr Arg Val Val Ser Val Leu Thr Val Leu
                                180                 185                 190

His Gln Asp Trp Leu Asn Gly Lys Glu Tyr Lys Cys Lys Val Ser Asn
                                195                 200                 205

Lys Ala Leu Pro Ala Pro Ile Glu Lys Thr Ile Ser Lys Ala Lys Gly
                            210                 215                 220

Gln Pro Arg Glu Pro Gln Val Tyr Thr Leu Pro Pro Ser Arg Glu Glu
                225                 230                 235                 240

Met Thr Lys Asn Gln Val Ser Leu Thr Cys Leu Val Lys Gly Phe Tyr
                                245                 250                 255

Pro Ser Asp Ile Ala Val Glu Trp Glu Ser Asn Gly Gln Pro Glu Asn
                                260                 265                 270

Asn Tyr Lys Thr Thr Pro Pro Val Leu Asp Ser Asp Gly Ser Phe Phe
                            275                 280                 285

Leu Tyr Ser Lys Leu Thr Val Asp Lys Ser Arg Trp Gln Gln Gly Asn
                            290                 295                 300

Val Phe Ser Cys Ser Val Met His Glu Ala Leu His Asn His Tyr Thr
                305                 310                 315                 320

Gln Lys Ser Leu Ser Leu Ser Pro Gly
                                325

<210> SEQ ID NO 29
<211> LENGTH: 5
<212> TYPE: PRT
<213> ORGANISM: artificial
<220> FEATURE:
<223> OTHER INFORMATION: CDR1 from heavy chain variable region
<220> FEATURE:
<221> NAME/KEY: misc
<222> LOCATION: (1)..(1)
<223> OTHER INFORMATION: Xaa can be any amino acid
<220> FEATURE:
<221> NAME/KEY: misc
<222> LOCATION: (1)..(1)
<223> OTHER INFORMATION: Xaa can be any amino acid
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (3)..(3)
<223> OTHER INFORMATION: Xaa can be any amino acid

<400> SEQUENCE: 29

Xaa Xaa Xaa Met Ala
1               5

<210> SEQ ID NO 30
<211> LENGTH: 17
```

```
<212> TYPE: PRT
<213> ORGANISM: artificial
<220> FEATURE:
<223> OTHER INFORMATION: CDR2 from heavy chain variable region
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (8)..(8)
<223> OTHER INFORMATION: Xaa can be any amino acid
<220> FEATURE:
<221> NAME/KEY: misc
<222> LOCATION: (9)..(9)
<223> OTHER INFORMATION: Xaa can K or T
<220> FEATURE:
<221> NAME/KEY: misc
<222> LOCATION: (10)..(10)
<223> OTHER INFORMATION: Xaa can be any amino acid
<220> FEATURE:
<221> NAME/KEY: misc
<222> LOCATION: (11)..(11)
<223> OTHER INFORMATION: Xaa can be any amino acid
<220> FEATURE:
<221> NAME/KEY: misc
<222> LOCATION: (16)..(16)
<223> OTHER INFORMATION: Xaa can be any amino acid
<220> FEATURE:
<221> NAME/KEY: misc
<222> LOCATION: (17)..(17)
<223> OTHER INFORMATION: Xaa can be any amino acid
<220> FEATURE:
<221> NAME/KEY: misc
<222> LOCATION: (17)..(17)
<223> OTHER INFORMATION: Xaa can be any amino acid

<400> SEQUENCE: 30

Ser Xaa Ser Tyr Asp Gly Ser Xaa Xaa Xaa Xaa Gly Asp Ser Val Xaa
1               5                   10                  15

Xaa

<210> SEQ ID NO 31
<211> LENGTH: 6
<212> TYPE: PRT
<213> ORGANISM: artificial
<220> FEATURE:
<223> OTHER INFORMATION: CDR3 from heavy chain variable region
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (5)..(5)
<223> OTHER INFORMATION: Xaa can be any amino acid
<220> FEATURE:
<221> NAME/KEY: misc
<222> LOCATION: (6)..(6)
<223> OTHER INFORMATION: Xaa can be any amino acid
<220> FEATURE:
<221> NAME/KEY: misc
<222> LOCATION: (6)..(6)
<223> OTHER INFORMATION: Xaa can be any amino acid

<400> SEQUENCE: 31

Ala Arg Xaa Gly Xaa Xaa
```

<210> SEQ ID NO 32
<211> LENGTH: 11
<212> TYPE: PRT
<213> ORGANISM: artificial
<220> FEATURE:
<223> OTHER INFORMATION: CDR1 from light chain variable region
<220> FEATURE:
<221> NAME/KEY: misc
<222> LOCATION: (1)..(1)
<223> OTHER INFORMATION: Xaa can be any amino acid
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (4)..(4)
<223> OTHER INFORMATION: Xaa can be any amino acid
<220> FEATURE:
<221> NAME/KEY: misc
<222> LOCATION: (5)..(5)
<223> OTHER INFORMATION: Xaa can be any amino acid
<220> FEATURE:
<221> NAME/KEY: misc
<222> LOCATION: (7)..(7)
<223> OTHER INFORMATION: Xaa can be any amino acid
<220> FEATURE:
<221> NAME/KEY: misc
<222> LOCATION: (8)..(8)
<223> OTHER INFORMATION: Xaa can be S or T
<220> FEATURE:
<221> NAME/KEY: misc
<222> LOCATION: (9)..(9)
<223> OTHER INFORMATION: Xaa can be any amino acid

<400> SEQUENCE: 32

Xaa Xaa Xaa Xaa Xaa Val Xaa Xaa Xaa Val Asp
 1               5                  10

<210> SEQ ID NO 33
<211> LENGTH: 7
<212> TYPE: PRT
<213> ORGANISM: artificial
<220> FEATURE:
<223> OTHER INFORMATION: CDR2 from light chain variable region
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (4)..(4)
<223> OTHER INFORMATION: Xaa can be T or N

<400> SEQUENCE: 33

Gly Xaa Xaa Xaa Arg Tyr Thr
 1               5

<210> SEQ ID NO 34
<211> LENGTH: 9
<212> TYPE: PRT
<213> ORGANISM: artificial
<220> FEATURE:
<223> OTHER INFORMATION: CDR3 from light chain variable region

```
<220> FEATURE:
<221> NAME/KEY: misc
<222> LOCATION: (1)..(1)
<223> OTHER INFORMATION: Xaa can be any amino acid
<220> FEATURE:
<221> NAME/KEY: misc
<222> LOCATION: (1)..(1)
<223> OTHER INFORMATION: Xaa can be any amino acid
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (4)..(4)
<223> OTHER INFORMATION: Xaa can be any amino acid
<220> FEATURE:
<221> NAME/KEY: misc
<222> LOCATION: (7)..(7)
<223> OTHER INFORMATION: Xaa can be any amino acid
<220> FEATURE:
<221> NAME/KEY: misc
<222> LOCATION: (8)..(8)
<223> OTHER INFORMATION: Xaa can be any amino acid
<220> FEATURE:
<221> NAME/KEY: misc
<222> LOCATION: (9)..(9)
<223> OTHER INFORMATION: Xaa can be any amino acid
<220> FEATURE:
<221> NAME/KEY: misc
<222> LOCATION: (9)..(9)
<223> OTHER INFORMATION: Xaa can be any amino acid

<400> SEQUENCE: 34

Xaa Xaa Xaa Xaa Asn His Xaa Xaa Xaa
1               5
```